(12) United States Patent
Mosel et al.

(10) Patent No.: US 6,579,266 B2
(45) Date of Patent: Jun. 17, 2003

(54) URINARY INCONTINENCE DIAGNOSTIC SYSTEM

(75) Inventors: Brian J. Mosel, Dublin, CA (US); Loren L. Roy, San Jose, CA (US); Frank W. Ingle, Palo Alto, CA (US); Stanley Levy, Saratoga, CA (US)

(73) Assignee: SURx, Inc., Livermore, CA (US)

( * ) Notice: Subject to any disclaimer, the term of this patent is extended or adjusted under 35 U.S.C. 154(b) by 72 days.

(21) Appl. No.: 09/851,662

(22) Filed: May 8, 2001

(65) Prior Publication Data

US 2001/0020162 A1 Sep. 6, 2001

Related U.S. Application Data

(60) Division of application No. 09/413,657, filed on Oct. 6, 1999, now Pat. No. 6,461,332, which is a continuation-in-part of application No. 60/153,332, filed on Sep. 10, 1999, which is a continuation-in-part of application No. 60/104,818, filed on Oct. 19, 1998, application No. 09/413,657, filed on Oct. 6, 1999, now Pat. No. 6,461,332, which is a continuation-in-part of application No. 09/288,865, filed on Apr. 9, 1999, now Pat. No. 6,416,504.

(51) Int. Cl.[7] .................................................. A61M 5/32
(52) U.S. Cl. ........................ 604/174; 600/561; 600/29
(58) Field of Search ........................ 604/93.01, 95.02, 604/96.01, 100.03, 103.5, 174, 179, 517, 264, 505, 349, 528, 544, 540, 599.04; 600/546, 566, 561, 591, 29, 587, 202; 607/96, 98–102, 113; 606/27–33, 108

(56) References Cited

U.S. PATENT DOCUMENTS

| | | | |
|---|---|---|---|
| 4,089,337 A | | 5/1978 | Kronner |
| 4,233,991 A | | 11/1980 | Bradley et al. |
| 4,397,647 A | * | 8/1983 | Gordon ...................... 604/180 |
| 4,484,585 A | | 11/1984 | Baier |
| 4,612,939 A | * | 9/1986 | Robertson .................. 128/774 |
| 4,652,259 A | | 3/1987 | O'Neil |
| 4,710,169 A | | 12/1987 | Christopher |
| 4,825,875 A | | 5/1989 | Ninan et al. |
| 5,318,541 A | | 6/1994 | Viera et al. |
| 5,334,159 A | | 8/1994 | Turkel |
| 5,389,100 A | | 2/1995 | Bacich et al. |
| 5,427,114 A | * | 6/1995 | Colliver et al. ............. 128/748 |
| 5,433,216 A | | 7/1995 | Sugrue et al. |
| 5,437,603 A | * | 8/1995 | Cerny et al. ................... 600/29 |

(List continued on next page.)

OTHER PUBLICATIONS

Kim et al., "The Vesico–Uethral Pressuregram Analysis of Urethral Function Under Stress", Journal of Biomechanics, vol. 30, p. 19 (1997).*

Kim et al., "The vesico–urethral pressuregram analysis of urethral function under stress" J. Biomechanics (1997) 30(1):19–25.

*Primary Examiner*—Brian L. Casler
*Assistant Examiner*—Jennifer Maynard
(74) *Attorney, Agent, or Firm*—Townsend Townsend & Crew LLP

(57) ABSTRACT

Devices, systems, and methods for diagnosing and/or treating urinary incontinence can accurately and reliably monitor both a vesicle pressure and a maximum urethral pressure of a patient during an abdominal pressure pulse so as to determine relationships between these pressures. Alignment between the location of maximum urethral pressure and a pressure sensor of a catheter can be maintained using an anchoring structure having a surface which engages a tissue surface along the bladder neck, urethra, or external meatus, which move with the urethra during abdominal pressure pulses. A pressuregram is generated graphically showing an increase in urethral pressure relative to an increase in vesicle pressure, and is often displayed in real time to a system operator adjacent the patient. Quantitative and/or qualitative diagnostic output allow selective remodeling of the patient's support structure so that the incontinence is inhibited.

21 Claims, 22 Drawing Sheets

U.S. PATENT DOCUMENTS

| | | | |
|---|---|---|---|
| 5,441,485 A | * 8/1995 | Peters | 604/101 |
| 5,460,606 A | 10/1995 | Daneshavar | |
| 5,566,680 A | 10/1996 | Urion et al. | |
| 5,637,074 A | * 6/1997 | Andino et al. | 600/29 |
| 5,653,683 A | * 8/1997 | D'Andrea | 604/21 |
| 5,653,705 A | 8/1997 | de la Torre et al. | |
| 5,690,645 A | 11/1997 | Van Erp | |
| 5,833,595 A | * 11/1998 | Lin | 600/29 |
| 5,833,666 A | * 11/1998 | Davis et al. | 601/180 |
| 5,891,457 A | 4/1999 | Neuwirth | |
| 5,964,732 A | 10/1999 | Willard | |
| 6,276,661 B1 | 8/2001 | Laird | |
| 6,292,700 B1 | * 9/2001 | Morrison et al. | 607/98 |
| 6,416,504 B2 | * 7/2002 | Mosel et al. | 604/528 |

* cited by examiner

```
PATIENT: Example
DATE:
++++++++++++
SURx         UPM         Ver 1.05
mid three little
TIME:08:20:13
SENSOR S/N=Y321
PU SENS.= 110.6031   PV SENS. 100.1075   PA SENS. 108.7434
ZERO;PU= -2.700271   PV=      -17.47311  PA=      -9.292039
PV              PU              PA
 24.73118       109.091         2.94E-07
 24.99999       109.091         2.94E-07
 24.46236       108.8209        2.94E-07
 24.99999       109.361         2.94E-07
 24.46236       109.091         2.94E-07
 24.99999       109.091         2.94E-07
 24.73118       109.091         2.94E-07
 24.73118       108.8209        2.94E-07
 24.73118       108.5509        2.94E-07
 24.73118       108.8209        2.94E-07
 24.73118       108.8209        2.94E-07
 24.73118       108.5509        2.94E-07
 24.73118       108.5509        2.94E-07
 24.73118       108.5509        2.94E-07
 24.73118       108.2809        2.94E-07
 24.46236       108.0108        2.94E-07
 24.73118       108.2809        2.94E-07
 24.46236       107.4708        2.94E-07
 24.99999       107.7408        2.94E-07
 24.73118       107.7408        2.94E-07
 24.99999       107.4708        2.94E-07
 24.73118       106.9307        2.94E-07
 24.99999       107.2008        2.94E-07
 24.73118       106.6607        2.94E-07
 25.26881       106.6607        2.94E-07
 24.73118       106.6607        2.94E-07
 24.99999       106.9307        2.94E-07
 24.73118       106.1207        2.94E-07
 25.26881       106.6607        2.94E-07
 24.73118       106.3907        2.94E-07
 24.99999       106.3907        2.94E-07
 24.73118       106.1207        2.94E-07
```

*FIG. 18.*

URINARY INCONTINENCE DIAGNOSTIC SYSTEM

CROSS-REFERENCES TO RELATED APPLICATIONS

This application is a divisional of U.S. patent application Ser. No. 09/413,657 filed Oct. 6, 1999, now U.S. Pat. No. 6,461,332, which claims the benefit and priority of U.S. Provisional Patent Application No. 60/153,332, filed Sep. 10, 1999 which claims the benefit and priority of U.S. Provisional Patent Application No. 60/104,818 filed Oct. 19, 1998. U.S. patent application Ser. No. 09/413,657 is a a CIP of U.S. patent application Ser. No. 09/288,865. filed Apr. 9, 1999 now U.S. Pat. No. 6,416,504. The subject matter of this application is related to that of U.S. Provisional Patent Application 60/153,330 filed Sep. 10, 1999, the disclosure of which is also incorporated herein by reference.

COPYRIGHT NOTICE

A portion of the disclosure of this patent document may contain material which is subject to copyright protection. The copyright owner has no objection to the xerographic reproduction by anyone of the patent document or the patent disclosure in exactly the form it appears in the Patent & Trademark Office patent file or records, but otherwise reserves all copyright rights whatsoever.

TECHNICAL FIELD

The present invention generally relates to devices, system, and methods for diagnosing and/or treating urinary incontinence. In an exemplary embodiment, the invention provides catheter-based pressure sensing systems for diagnosing female urinary incontinence, and in particular, provides systems for determining the relationship between urethral pressure and vesicle pressure in response to changes in abdominal pressure. Preferred aspects of the present invention relate to urethral catheter holder mechanisms.

BACKGROUND OF THE INVENTION

Urinary incontinence arises in both men and women with varying degrees of severity, and from different causes. In men, the condition most frequently occurs as a result of prostatectomies which result in mechanical damage to the urethral sphincter. In women, the condition typically arises after pregnancy when musculoskeletal damage has occurred as a result of inelastic stretching of the structures which support the genitourinary tract. Specifically, pregnancy can result in inelastic stretching of the pelvic floor, the external sphincter, and the tissue structures which support the bladder and bladder neck region. In each of these cases, urinary leakage typically occurs when a patient's abdominal pressure increases as a result of stress, e.g., coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt a behavior modification intended to reduce the incidence of urinary leakage.

In cases where such non-interventional approaches are inadequate or unacceptable, the patient may undergo surgery to correct the problem. A wide variety of procedures have been developed to correct urinary incontinence in women. Several of these procedures are specifically intended to support the bladder neck region. For example, sutures, straps or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

In work related to the present invention, it has recently been proposed to treat incontinence by directing energy to a tissue structure comprising or supporting the patient's urethra, bladder neck, or bladder. The energy can contract collagenous structures such as fascia, tendons, or the like, increasing the structural support of these natural support tissues. As described in PCT Application Ser. Nos. 98/16754 and 97/20191, the full disclosures of which are incorporated herein by reference, the energy may be transmitted through an intermediate tissue, or by accessing the collagenous tissue surface in a minimally invasive manner.

Researchers have studied female urinary incontinence by evaluating the relationship between a patient's urethral pressure and her vesicle (i.e.:, bladder) pressure. In an article by Kim et al., The Vesico-Urethral Pressuregram Analysis of Urethral Function Under Stress, *Journal of Biomechanics*, Vol. 30, page 19 (1997), proposed a method for analyzing the interaction between the vesicle pressure and urethral pressure to assess urinary stress incontinence. Both urethral pressure and vesicle pressure will change in response to changes in abdominal pressure. However, the urethral and vesicle pressures may change at different rates as the abdominal pressure changes. Incontinence may occur when the vesicle pressure exceeds the urethral pressure. Hence, incontinence can be studied by producing a pressuregram showing the relationship between the urethral pressure and the vesicle pressure of the patient during abdominal pressure pulses.

A patient's vesicle and urethral pressures can be measured by introducing a catheter into the urethra and positioning pressure sensors of the catheter at the desired measurement sites in the urethra and/or bladder. The measurements of the patient's vesicle and urethral pressures are preferably taken simultaneously during changes in abdominal pressures.

Unfortunately, simultaneous pressure measurements can be difficult to obtain using presently available pressure-sensing catheters. Hence, existing systems are not well suited for diagnosing urinary incontinence of a particular patient. Similarly, while the recently proposed tissue contraction therapies offer great promise for treatment of urinary stress incontinence, proper treatment to enhance elongated or weak support structures of a particular patient could benefit significantly from improved techniques for diagnosing urinary incontinence.

In light of the above, it would be desirable to provide improved devices, systems, and methods for diagnosing and/or treating urinary incontinence.

SUMMARY OF THE INVENTION

The present invention generally provides improved devices, systems, and methods for diagnosing and/or treating urinary incontinence. The invention provides pressure-sensing catheter systems which can accurately and reliably monitor both a vesicle pressure and a maximum urethral pressure of a patient during an abdominal pressure pulse so as to determine relationships between these pressures. Work in connection with the invention has shown that diagnostic urethral pressure measurements during a pressure pulse are sensitive to loss of alignment between the pressure sensor and the target pressure location. Advantageously, alignment between, for example, the location of maximum urethral pressure and a pressure sensor of a catheter can be maintained using an anchoring structure having a surface which engages a tissue surface along the bladder neck, urethra, or external meatus (the tissue structure adjacent the urethral opening). These tissues generally moves with the urethra during abdominal pressure pulses, so that the anchoring structure will often move the pressure sensor when an abdominal pressure pulse is induced. The invention allows a reliable, accurate pressuregram to be generated, the pressuregram graphically showing an increase in urethral pressure relative to an increase in vesicle pressure. This pressuregram will ideally be displayed in real time to a system operator adjacent the patient, and may provide a quantitative and/or qualitative diagnostic output allowing selective remodeling of the patient's support structure so that the incontinence is inhibited.

In a first aspect, the invention provides an apparatus for evaluating urinary incontinence of a patient. The patient has a urethra extending from a bladder to a urethral opening, with a maximum urethral pressure disposed between the bladder and opening. The system comprises a pressure-sensing system including an elongate body having a proximal end and a distal end. A vesicle pressure sensor is disposed adjacent the distal end for measuring fluid pressure within the bladder. At least one urethral pressure sensor is disposed proximally of the vesicle pressure sensor for measuring urethral pressure. An anchoring structure is disposed along the elongate body. The anchoring structure is adapted to engage a tissue surface adjacent the urethra so as to maintain alignment between the urethral pressure sensor and the maximum urethral pressure when a pressure pulse moves the urethra. A processor is coupled to the pressure-sensing system. The processor calculates a relationship between the urethral pressure and the vesicle pressure.

Typically, the calculated relationship will comprise a pressuregram which is shown on a display in real time to a system operator disposed adjacent the patient. The pressuregram will typically include a slope defined by an increase of the measured vesicle pressure relative to an increase of the measured urethral pressure. Such pressuregram may be calculated from a plurality of pressure pulses, and will typically be independent of time. The pressuregram may be displayed in a variety of formats, including plotting simultaneous pressure data pairs taken simultaneously in the urethra and the bladder, with vesicular pressure along a horizontal axis and urethral pressure along a vertical axis or vice-versa.

The anchoring structure will often comprise a radially expandable structure, the expandable structure preferably having at least one channel allowing free transmission of urine through the urethra when expanded. Suitable expandable structures include balloons having multiple lobes defining the channel therebetween. The expandable structure may expand within the urethral passage to engage the surrounding tissues, or may be inserted and expanded beyond the urethra so that a proximally oriented surface of the expandable structure engages the bladder. In many embodiments, a distally oriented surface will be positionable along the elongate body to engage an external meatus so as to substantially affix the urethral pressure sensor relative to the maximum urethral pressure location.

The anchoring structure may comprise at least one vacuum port disposed along the elongate body and oriented to engage a tissue along the urethra. When a vacuum is applied to the vacuum port, the vacuum port can safely secure the urethral pressure sensor at the desired position within the urethra. In some embodiments, a plurality of urethral pressure sensors may be distributed axially so as to reduce sensitivity of the pressure sensor system to movement relative to the surrounding urethra.

The present invention also provides a urethral catheter holder which is adapted to support a pressure-sensing catheter such that the catheter can be positioned along the patient's urethra. The holder can generally maintain alignment with a maximum urethral pressure by allowing the catheter to move in response to urethral movement such that a pressure-sensing transducer disposed on the catheter does not move relative to the urethra when the patient coughs.

In a preferred aspect of the present invention, the urethral catheter holder comprises a supporting base, which is adapted to register against the labia of the patient; a suspension housing mounted to the supporting base; a catheter securement device, (which is adapted to move within the suspension housing when the patient coughs such that the catheter moves with the urethra); and a biasing device. In preferred aspects, the catheter securement device comprises a catheter guide which is adapted to contact against the external meatus of the patient's urethra. The biasing device operates to provide a preloading force on the catheter guide, thereby holding the catheter guide against the external meatus of the patient's urethra such that the catheter securement device moves with the movement of the urethra. Additionally, the biasing device operates to push the catheter securement device against the supporting base, thereby minimizing unwanted motion of the catheter securement device within the suspension housing.

The catheter securement device is adapted to support the catheter in a manner such that the catheter moves in response to movement of the urethra, with the catheter remaining in generally the same position relative to the surrounding urethra when the patient coughs. In a preferred aspect, the catheter securement device comprises a torroidal balloon, a generally ring-shaped balloon support mount surrounding the torroidal balloon and a pneumatic or hydraulic pressure tube for inflating or deflating the torroidal balloon. The catheter passes longitudinally through the catheter holder and is received through the orifice defined by the torroidal balloon. Inflation of the torroidal balloon will cause it to expand radially inwardly such that it's central orifice contracts, thereby gently pushing against the sides of the catheter.

In other preferred aspects of the invention, the catheter securement device comprises a mechanical clamp which is mounted to move longitudinally within the suspension housing.

Optionally, the present urethral catheter holder may also comprise a pair of leg straps, which can be wrapped around the patient's thighs, (or a stretchable undergarment with leg straps attachable thereto), such that the supporting base of the catheter holder can be held at a generally fixed position against the labia of the patient. An advantage of such leg straps is that pressure measurements can then be taken easily with the patient in different positions, including supine and sitting. An additional advantage of the present system is that it allows hands-free operation for the clinician.

In another aspect, the invention provides a data system for use with a mechanism for diagnosing urinary incontinence of a patient. The mechanism produces a pressuregram indicating a pressuregram slope defined by a change of urethral pressure of the patient relative to a change of vesicle pressure of the patient. The vesicle and urethral pressures are measured with a catheter system having a proximal end and a distal end. The data system comprises a processor coupled to the catheter for receiving a vesicle pressure signal and urethral pressure signal. The processor generates a pressuregram dataset in real time. At least in part from the vesicle and urethral pressure signals. A display is coupled to the processor so as to generate a real time image of the pressuregram from the pressuregram dataset. The display is visible from adjacent the proximal end of the catheter.

Generally, a soft tissue of the patient moves with the urethra during a pelvic pressure pulse. Suitable pressure pulses can be induced by having the patient cough, by having the patient perform the Valsalva maneuver, by pushing manually or with an impulse device against the abdomen, or the like. To accommodate the resulting tissue movement, the system will often include a catheter positioning surface attached to the catheter. The catheter positioning surface will be adapted to engage the soft tissue so as to inhibit movement of the catheter within the urethra. In some embodiments, the positioning surface may be insertable along at least a portion of the urethra. Such positioning surface include high friction outer catheter surfaces, surfaces surrounding vacuum ports, atraumatic balloons, and the like. Optionally, some mechanism for facilitating insertion and removal of the catheter may be provided, such as a low friction interface sheath, or the like.

Alternative embodiments may include positioning surfaces which are larger in cross-section than the catheter so as to engage a soft tissue beyond the urethra, such as an external meatus, bladder, or the like, with such large positioning surfaces often being adjustably affixable along an axis of the catheter to facilitate positioning of the urethral pressure sensor at the point of maximum urethral pressure. In such embodiments, a biasing mechanism will often support the positioning surface against the external meatus, the support often reacting against a reaction support such as leg straps, a garment, or the like. The biasing mechanism will preferably allow at least about 2 cm of movement of the external meatus and catheter without altering the alignment of the urethral pressure sensor.

The processor will preferably selectably display one or more pressure pulses, and will ideally be selectably capable of refreshing the display between pressure pulses. An exemplary processor extrapolates an equilibrium pressure (above which the vesicle pressure exceeds the urethral pressure) using a curve approximation of the pressuregram.

In yet another aspect, the invention provides a system for treatment of urinary stress incontinence of a patient. The patient has a tissue comprising or supporting the urethra, the bladder neck, or the bladder. The system comprises a diagnostic system including a urethral pressure sensor, a bladder pressure sensor, and a processor coupled to the sensors. The processor generates an output indicating a desired remodeling of the tissue of the patient. A probe has an energy-transmitting element that controllably delivers energy to the tissue so as to effect the desire remodeling such that incontinence is inhibited.

In some embodiments, the probe may be used to controllably deliver the energy in response to the output of the processor. Optionally, the processor may be coupled to the probe and may provide an energy signal to the probe so as to control the delivered energy.

In another method aspect, the invention provides a method for treating urinary stress incontinence of a patient. The method comprises sensing a bladder pressure and a urethral pressure. A desired remodeling of a tissue comprising or supporting a urethra, a bladder neck, and/or a bladder of the patient is determined from the bladder pressure and the urethral pressure. The desired remodeling of the tissue is effected so that incontinence is inhibited.

Typically, a pressure pulse will be generated during the sensing step. The pressure pulse may, in some embodiments, be generated after effecting partial remodeling of the tissue for use as feedback during the remodeling step.

In yet another method aspect, the invention provides a method for treatment of urinary stress incontinence of a patient. A pressuregram of the patient indicates a urethral pressure of the patient which differs from a vesicle pressure of the patient by a continence margin. The pressuregram has a pressuregram slope defined as a change of the vesicle pressure relative to a change of the urethral pressure. The pressuregram slope is such that the vesicle pressure will exceed the urethral pressure of the patient above an equilibrium pressure. The method comprises determining a desired change in a support tissue comprising or supporting the urethra based at least in part on the equilibrium pressure, the continence margin, and/or the pressuregram slope. The support tissue is remodeled per the desired change.

The remodeling step may comprise directing energy into the support tissue so as to contract the support tissue. Often times, a plurality of pressuregrams will be taken with the patient in different positions, such as standing, sitting, supine, and the like, for determining the desired change.

In yet another aspect, the invention provides a system for evaluating urinary incontinence. The system comprises a body having a proximal end, a distal end, and a cross-section suitable for insertion into a urethra. A pressure sensor is disposed along the body for measuring urethral pressure, and a position sensing system or means is couplable to the body to measure an axial position of the pressure sensor within the urethra.

BRIEF DESCRIPTION OF THE DRAWINGS

FIG. 18 is a portion of a pressuregram dataset measured using the pressure measurement system.

DESCRIPTION OF THE SPECIFIC EMBODIMENTS

Figure 1:
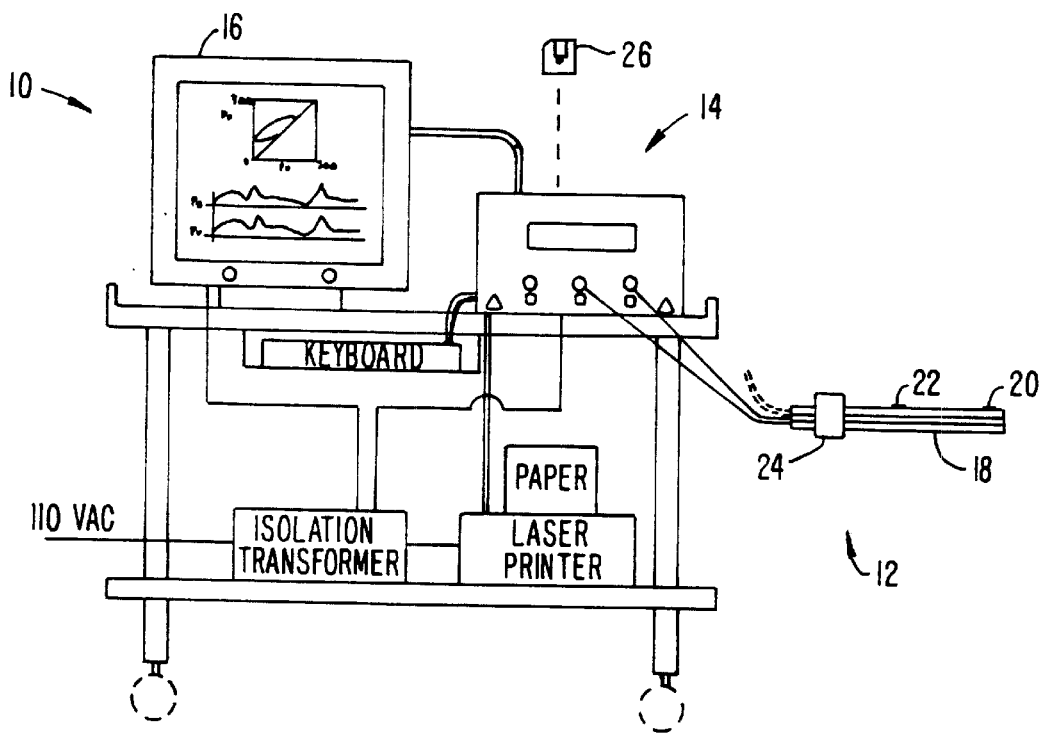
FIG. 1 is a schematic illustration of a system for diagnosing urinary stress incontinence according to the principles of the present invention.

Referring first to FIG. 1, an exemplary diagnostic system 10 for evaluating urinary incontinence generally includes a pressure measurement system 12, a processor 14, and a display 16. Pressure measurement system 12 includes a pressure measurement catheter 18 including a distal vesicle pressure sensor 20 and a more proximal urethral pressure sensor 22. An anchoring structure 24 maintains alignment between urethral pressure sensor 22 and a target location of the urethra by engaging a soft tissue adjacent the urethra, as will be described in detail below.

Processor 14 may include an embedded personal computer (PC) running programming embodying the methods of the present invention in a tangible machine readable medium. A wide variety of tangible media are encompassed by the present invention, such as a floppy disk 26, a hard disk, an optical disk, a non-volatile memory, or the like. In some embodiments, the programming may be downloaded via a data transmission system such as an Ethernet, an internet or intranet, or the like. Processor 14 will preferably run the programming on a Windows™ operating system, and may optionally use commercially available data manipulation programs such a Excel™, or the like. The processor typically comprises a commercially available PC such as an IBMT™ clone, Pentium™, or the like. Display 16 will generally comprise a standard commercially available VGA monitor, or the like.

Figure 2:
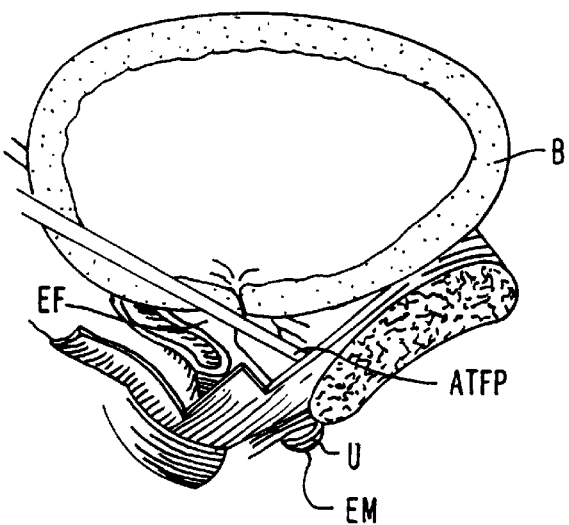
FIG. 2 shows a cut-away view of tissues supporting the bladder, bladder neck, and urethra.

Some of the tissue structures which support the urethra are illustrated in FIG. 2. This drawing shows the pelvic support tissues which generally maintain the position of much of the genitourinary tract, and particularly the position of urinary bladder B. Of particular importance for the method of the present invention, endopelvic fascia (EF) may define a hammock-like structure which extends laterally between the left and right arcus tendinous fascia pelvis (ATFP). These later structures may extend substantially between the anterior and posterior portions of the pelvis, so that the endopelvic fascia (EF) largely defines the pelvic floor.

The fascial tissue of the pelvic floor may comprise tissues referred to under different names by surgeons of different disciplines, and possibly even by different practitioners within a specialty. In fact, some surgeons may assign the collagenous support structure referred to herein as the endopelvic fascia one name when viewed from a superior approach, and a different name when viewed from an inferior approach. Some or all of this support structure may comprise two collagenous layers with a thin muscular layer therebetween, or may comprise a single collagenous layer. In general terms, the diagnostic and treatment techniques of the present invention may be directed toward any of the collagenous portions of the support structures for the urethra, bladder neck, and bladder. Hence, the tissues of interest may include and/or be referred to as endopelvic fascia, arcus tendinous fascia pelvis, urethropelvic ligaments, periurethral fascia, levator fascia, vesicopelvic fascia, transversalis fascia, and/or vesicle fascia, as well as other collagenous support structures.

In women with urinary stress incontinence due to bladder neck hypermobility, the bladder has typically dropped between about 1.0 cm and 1.5 cm (or more) below its nominal position. This condition is typically due to weakening and/or stretching of the pelvic support tissues, including the endopelvic fascia, the arcus tendinous fascia pelvis, and the surrounding ligaments and muscles, often as a result of bearing children. When a woman with urinary stress incontinence sneezes, coughs, laughs, or exercises, the abdominal pressure often increases momentarily. Such pressure pulses force the bladder to descend still farther, shortening or misaligning the urethra UR and momentarily opening the urinary sphincter. The tissues adjacent the urethral opening are generally referred to as the external meatus EM.

Figure 3A:
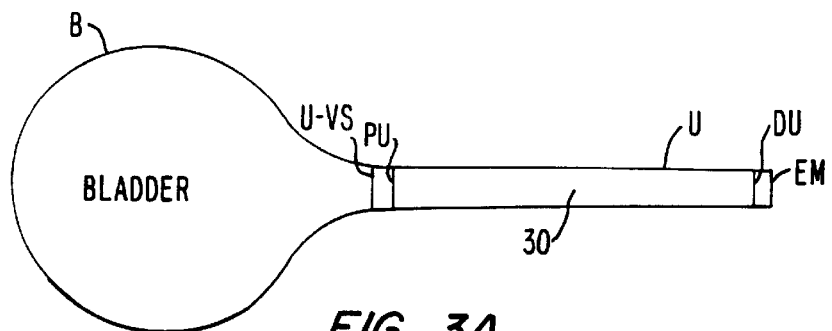
FIGS. 3A and B schematically show target pressure measurement locations along the urethra, and illustrate the sensitivity of pressuregram measurements to loss of alignment with the location of maximum urethral pressure.

Locations along urethra U targeted for pressure measurement can be understood with reference to FIGS. 3A and B. In general, a patient remains continent when a maximum urethral pressure Pm along urethra U is larger than a vesicle pressure Pv. It should be noted that when describing the structures of the urethra and adjacent tissues, the portions adjacent bladder B are considered proximal, while the portions adjacent external meatus EM are considered distal. With this in mind, pressure within bladder B is substantially uniform, while the urethral pressure rises distally between a urethro-vesicular junction U-VJ and an adjacent proximal urethra PU. Similarly, pressure will rise proximally from the external meatus EM to the adjacent distal urethra DU. A location 30 of the maximum urethral pressure Pm will be between these ends. While maximum pressure location 30 is commonly referred to as the mid-urethra, and maximum pressure Pm is commonly referred to as the mid-urethral pressure, it should be understood that this location need not necessarily be disposed at the geometrical midpoint of the urethral passage. It should also be understood that the corresponding catheter structures and their movement within the urethra will be described with reference to a distal orientation extending from the external meatus inward toward the bladder.

Figure 3B:
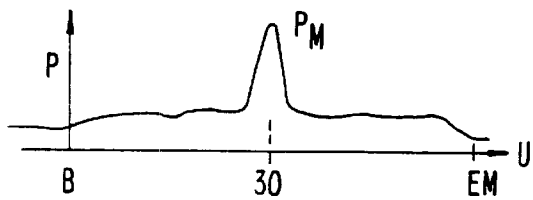

As schematically illustrated in FIG. 3B, the maximum urethral pressure Pm is quite limited in length along the axis of urethra U, the enhanced pressure often having a width in a range from about 3 to about 5 mm. Consequently, any significant movement of a pressure sensor from the maximum pressure location 30 could lead to substantial measurement errors. As urethral pressure measurements will preferably be taken during abdominal pressure pulses, and as such pressure pulses can cause the soft tissues along urethra U to move significantly, anchoring structure 24 can significantly enhance measurement accuracy and reliability by inhibiting movement between the pressure sensor and the target location 30.

Figure 4:
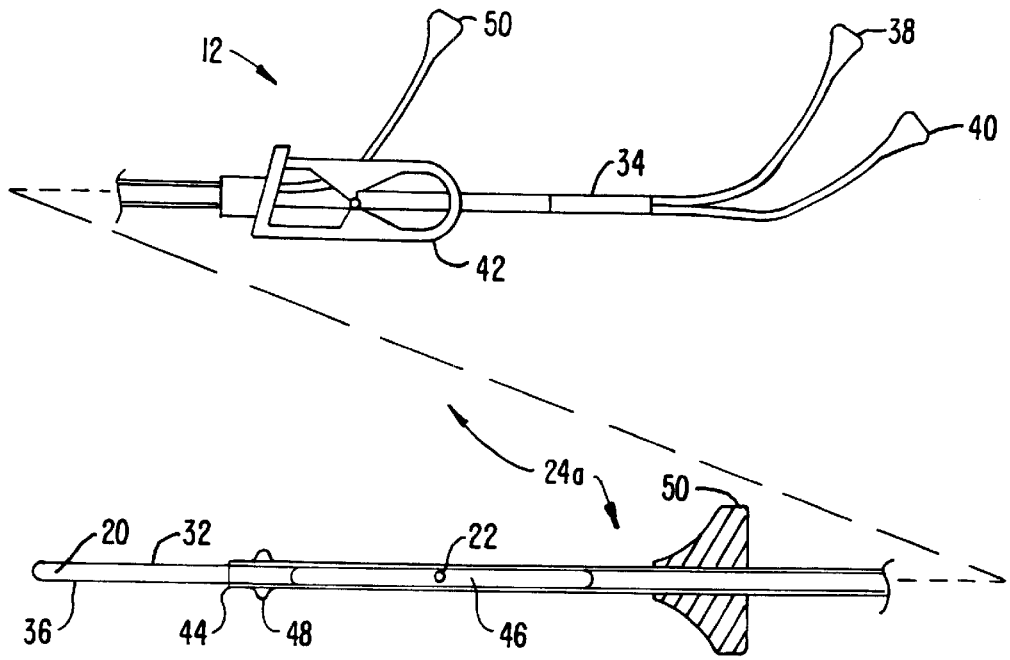
FIG. 4 schematically illustrates an exemplary pressure measurement system for use in the diagnostic system of FIG. 1, the pressure measurement system including a pressure measurement catheter and an anchoring structure.

An exemplary pressure sensing system 12 can be seen more clearly in FIG. 4. Pressure sensing catheter 18 comprises an elongate body 32 with a proximal end 34 and a distal end 36. Vesicular pressure sensor 20 is disposed adjacent distal end 36, and may optionally comprise a port opening to a fluid lumen in communication with a pressure transducer, which may be mounted along catheter body 32, adjacent proximal end 34, or even be incorporated into processor 14. Alternative pressure sensors which may be suitable include solid state piezo-resistive transducers mounted at the sensor port location, optical pressure sensors, and the like. Urethral pressure sensor 22 may similarly comprise any of a variety of alternative sensor structures, typically comprising a structure similar to that of the vesicle pressure sensor. A urethral sensor coupler 38 and a vesicular sensor coupler 40 detachably couple the pressure sensors to processor 14, using fluid, optical, or electrical signals to transmits pressure information to the processor as appropriate for the sensor structures.

Catheter 18 may comprise a specialized multi-lumen structure having an outer diameter in a range from about 4 Fr to about 14 Fr fabricated from a suitable polymer. Typical total lengths for urethra U will be about 3–5 cm for women, and the length between urethral pressure sensor 22 and both vesicle pressure sensor 22 and proximal end 34 will typically be at least 5 cm to allow simultaneous bladder and urethral pressure measurements throughout the urethra. Catheter 18 may comprise or be modified from an off-the-shelf dual pressure sensing catheter such as those sold by Life Tech under the model name Triple Lumen Urinary Catheter™, by GAELTEC under the name Dual Transducer Micro-Tip Catheter™, or the like. Suitable fluid transducers for use with fluid coupling catheters include the disposable medical pressure transducers sold by UTAH MEDICAL under the name Delta I™ or Deltran I™.

Urethral pressure sensor 22 of catheter 18 may be held in alignment with an anchoring sheath 24a. Sheath 24a has a lumen which extends from a proximal clamp 42 to a distal port 44, the lumen slidingly receiving catheter 18. Clamp 42 can releasably affix catheter 18 to sheath 24a. An elongate opening 44 through the wall of sheath 24a exposes urethral pressure sensor 22 throughout a range of catheter positions. Sheath 24a has a length less than that of catheter 18, and will typically have an inner diameter in a range from about 4 Fr to about 14 Fr so as to receive the catheter therein. Sheath 24a will typically comprise a polymer, often comprising a multi lumen high strength biocompatible polymer structure commercially available from a variety of sources.

Anchoring sheath 24a includes a distal balloon 48 which is in fluid communication with a balloon inflation coupler 50 via a balloon inflation lumen of the sheath. Balloon 48 may optionally have an expanded diameter larger than that of the urethra, the balloon generally being rounded and conforming to the shape of the bladder neck so that a proximal surface of the balloon engages the soft tissue of the bladder adjacent the urethra. Alternative balloon designs may have multiple lobes so as to define channels between the balloon surface and the engaged tissue, as will be described below. Such channels may be defined by two-sided balloons or balloons having a winged configuration, and help to avoid impeding of the natural flow of urine during urodynamic exams.

Balloon 48 is inserted in a low profile configuration through urethra U, inflated within the bladder via balloon port 50, and engages the bladder neck to inhibit proximal movement of the sheath. A simple washer 50 is slidable over sheath 24a by hand, and frictionally resists movement when in position. Washer 50 has a distally oriented surface which may be conical (as shown in FIG. 4) planer, or the like, and will preferably comprise a soft, compliant polymer such as a rubber or the like to reduce patient discomfort. Once sheath 24a is positioned with balloon 48 engaged against the bladder neck, washer 50 can be slid against the external meatus, thereby clamping the urethra between the proximally oriented surface of the balloon and the distally oriented surface of the washer, effectively inhibiting movement of the sheath relative to the urethra.

As catheter 18 can slide within the lumen of sheath 24a while urethral sensor 22 is exposed through opening 46, the pressure sensor can be accurately positioned at target location 30 by moving the catheter axially while viewing a display indicating the pressure at the urethral sensor in real time. Once the displayed pressure is at its maximum, catheter 18 can be axially affixed to sheath 24a, and hence to the urethra, using clamp 42. Preferably, clamp 42 will not be tightened sufficiently to inhibit transmission of pressure signals if fluid coupling is used. Clamp 42 may comprise a simple ratcheted compression device, although a variety of latches, threaded chocks, and other motion-inhibiting structures might be used.

Figure 5:
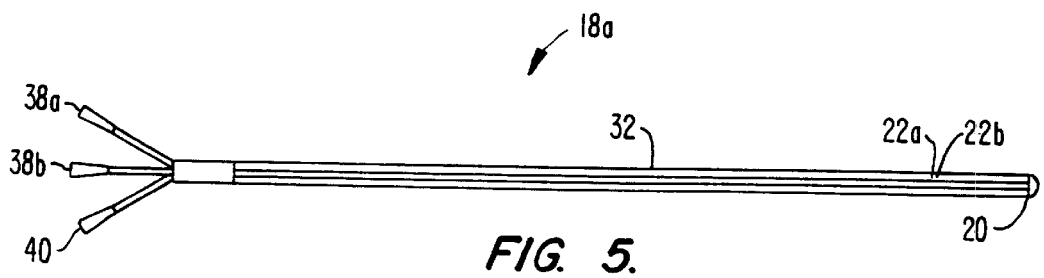
FIG. 5 schematically illustrates a pressure measurement catheter for use in the pressure measurement system of FIG. 4.

Referring now to FIG. 5, a closely related catheter 18a includes first and second urethral pressure ports 22a, 22b spaced axially along catheter body 32, preferably having an axial separation in a range from about 1 mm to about 10 mm between the urethral pressure ports. Each urethal pressure port is independently coupled to an associated urethral pressure coupler 38a, 38b via an associated lumen for measuring the local urethral pressure adjacent the associated port. Processor 14 will preferably be capable of deriving the pressuregram by selectively using the highest of the pressures indicated by any of the pressure ports. Hence, by including a plurality of axially separated ports, the sensitivity of the system to axial movement of the catheter within the urethra can be decreased. In alternative embodiments, a catheter body lumen which provides fluid coupling with a vesical port may be used to at least partially fill bladder B in preparation for urodynamic testing.

Figure 6B:
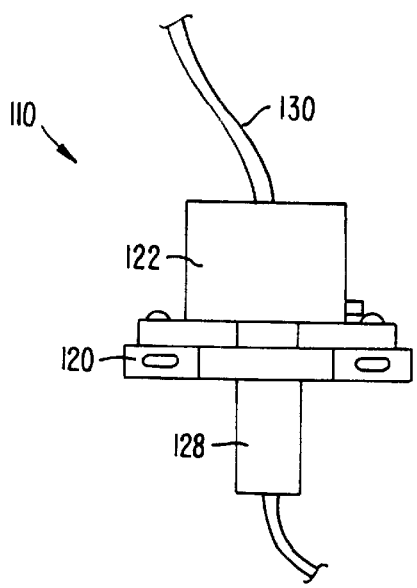
FIG. 6B is a front view of the urethral catheter holder of FIG. 6.
Figure 6A:
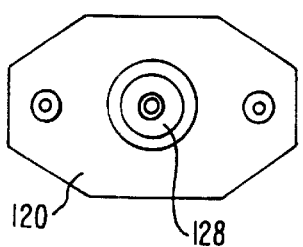
FIG. 6A is a top view of the urethral catheter holder of FIG. 6.
Figure 6:
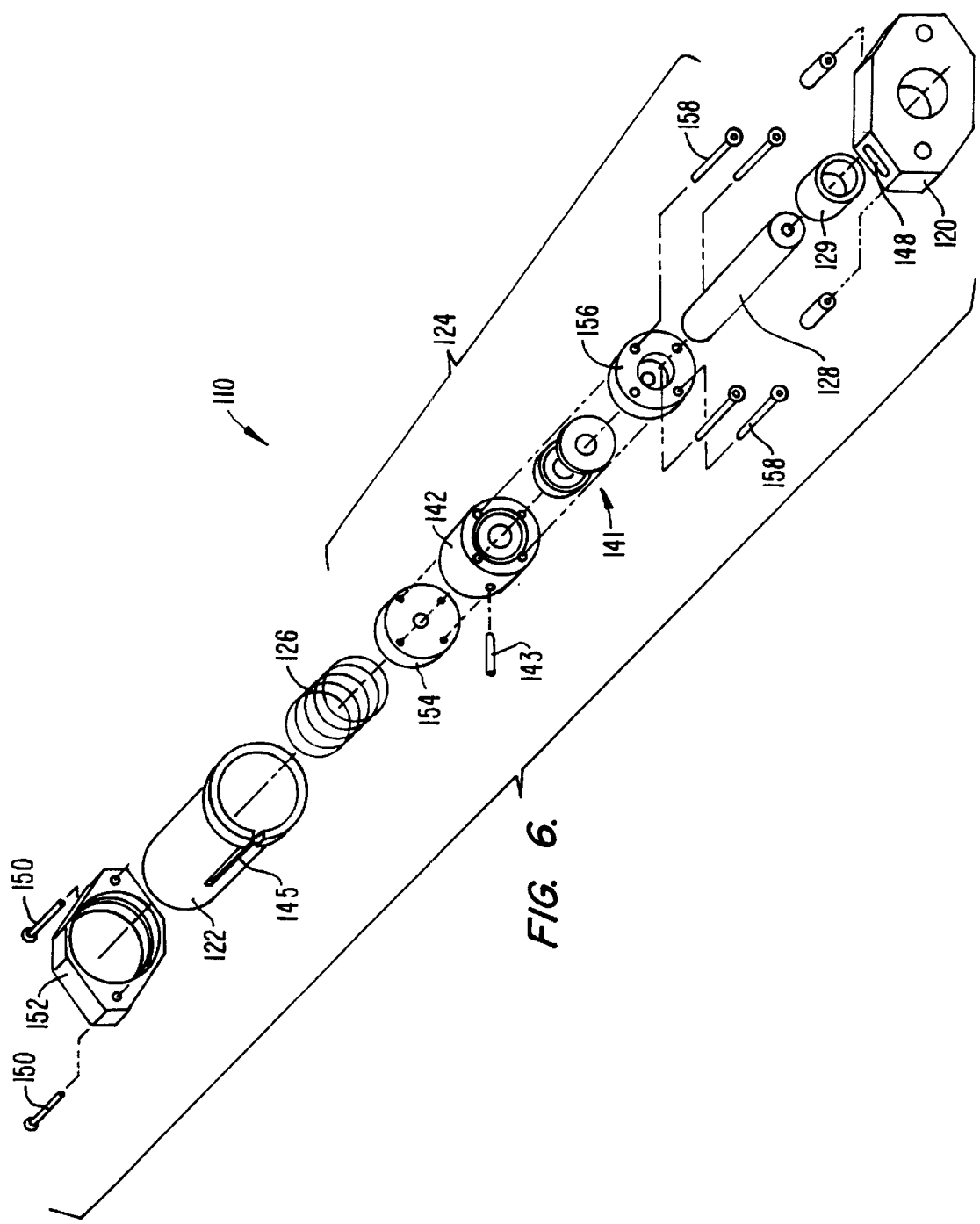
FIG. 6 is an exploded view of an alternative anchoring structure for use in the pressure measurement system of FIG. 4, here in the form of a urethral catheter holder.

In another aspects of the present invention, a urethral catheter holder is provided. FIG. 6 shows an exploded view of the assembly of urethra catheter holder 110, comprising a supporting base 120, a suspension housing 122, a catheter securement device 124, a biasing element 126, and a catheter guide 128. Assembled views of catheter holder 110 are shown in FIGS. 6A, 6B, 6C, and 6D. As shown in FIG. 6A, a catheter 130 is received longitudinally through catheter holder 110, as shown.

Catheter holder 110 is adapted to hold catheter 130 such that supporting base 120 can remain in contact with the patient's labia while catheter 130 moves longitudinally in response to movement of the patient's urethra when the patient coughs. Accordingly, one advantage of the present invention is that catheter 130 can be positioned to remain in at the same relative location with respect to the patient's urethra when the patient coughs. The ability of catheter securement device 124 to hold catheter 130 to allow for catheter movement in response to urethra movement, without tightly pinching catheter 130 is accomplished by the present novel catheter securement system, as follows.

Figure 6C:
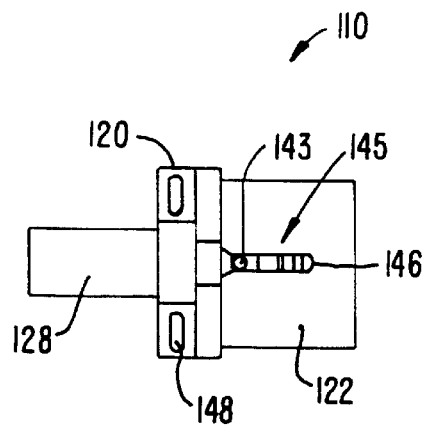
FIG. 6C is a right-side view of the urethral catheter holder of FIG. 6.
Figure 6D:
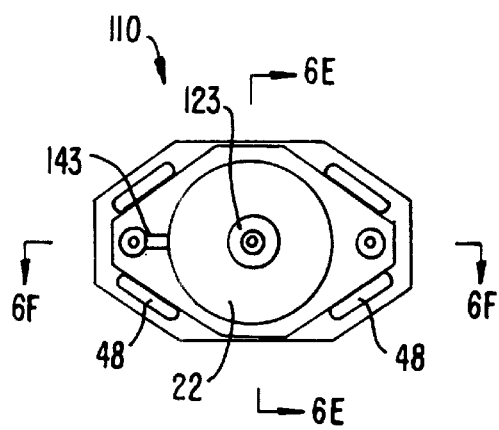
FIG. 6D is a rear view of the urethral catheter holder of FIG. 6.
Figure 6E:
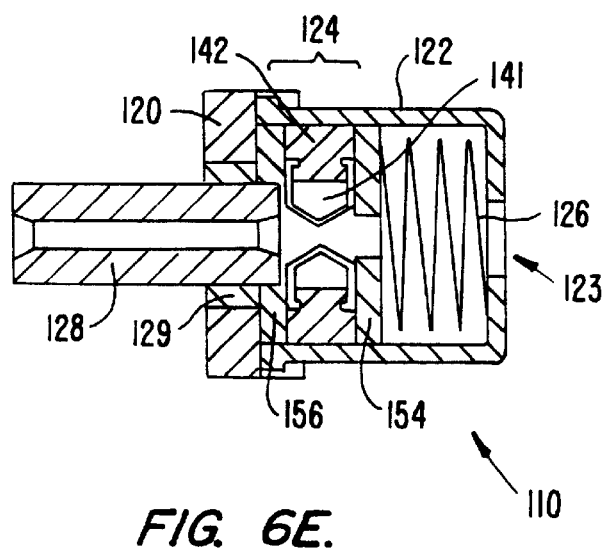
FIG. 6E is a sectional plan view of the urethral catheter holder taken along line 6E—6E in FIG. 6D.
Figure 6F:
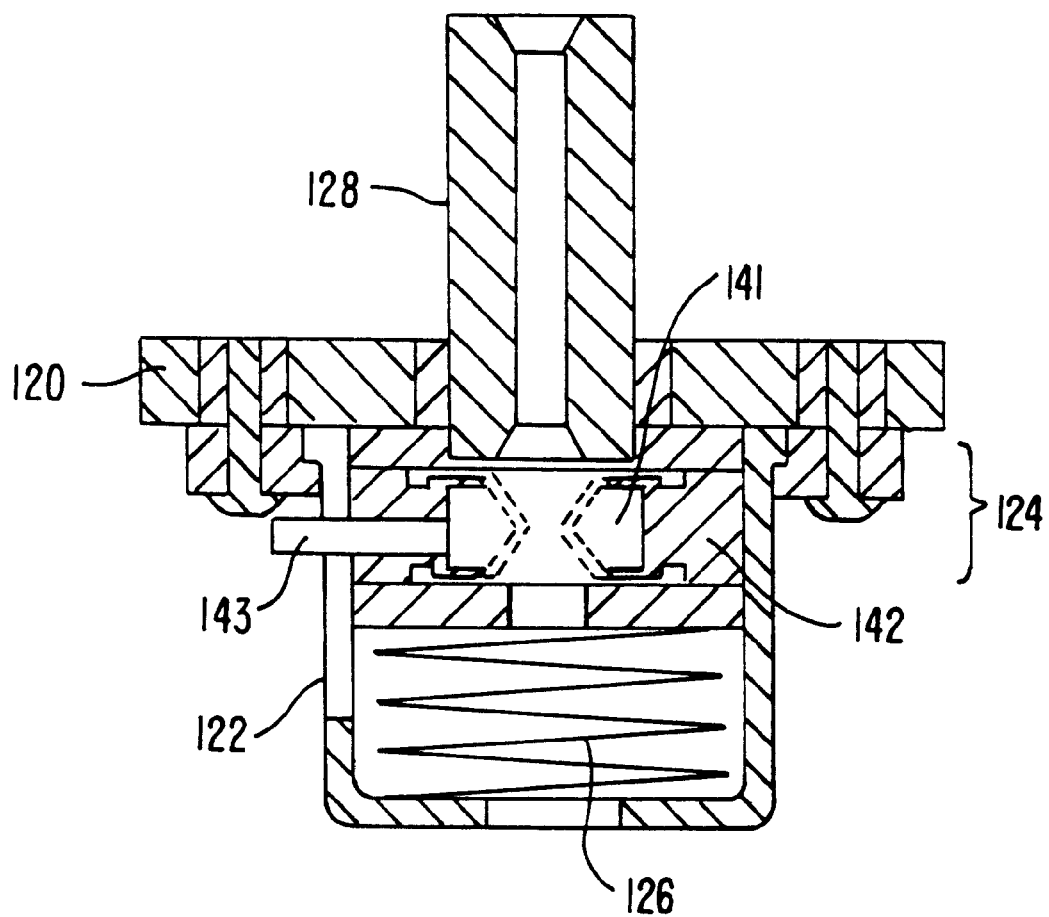
FIG. 6F is a sectional elevation view of the urethral catheter holder taken along line 6F—6F in FIG. 6D.

Referring to FIGS. 6E and 6F, catheter securement device 124 preferably comprises a torroidal balloon 141, a generally ring-shaped balloon support mount 142, a pneumatic or hydraulic pressure tube 143, and a catheter guide 128, as shown. Together, torroidal balloon 141, balloon support 142, pressure tube 143, and catheter guide 128 are adapted to slide longitudinally as a unit within the suspension housing 122. A bushing 129, which may be made of Teflon, is provided to enable catheter guide 128 to slide freely through supporting base 120. Biasing element 126, which may preferably comprise a mechanical spring, provides a preloading force which gently pushes catheter guide 128 against the external meatus EM of the patient's urethra 150, (see FIG. 10). Accordingly, catheter guide 128 will move together with the patient's urethra such that catheter guide 128 identically tracks the movement of urethra 150.

Figure 7:
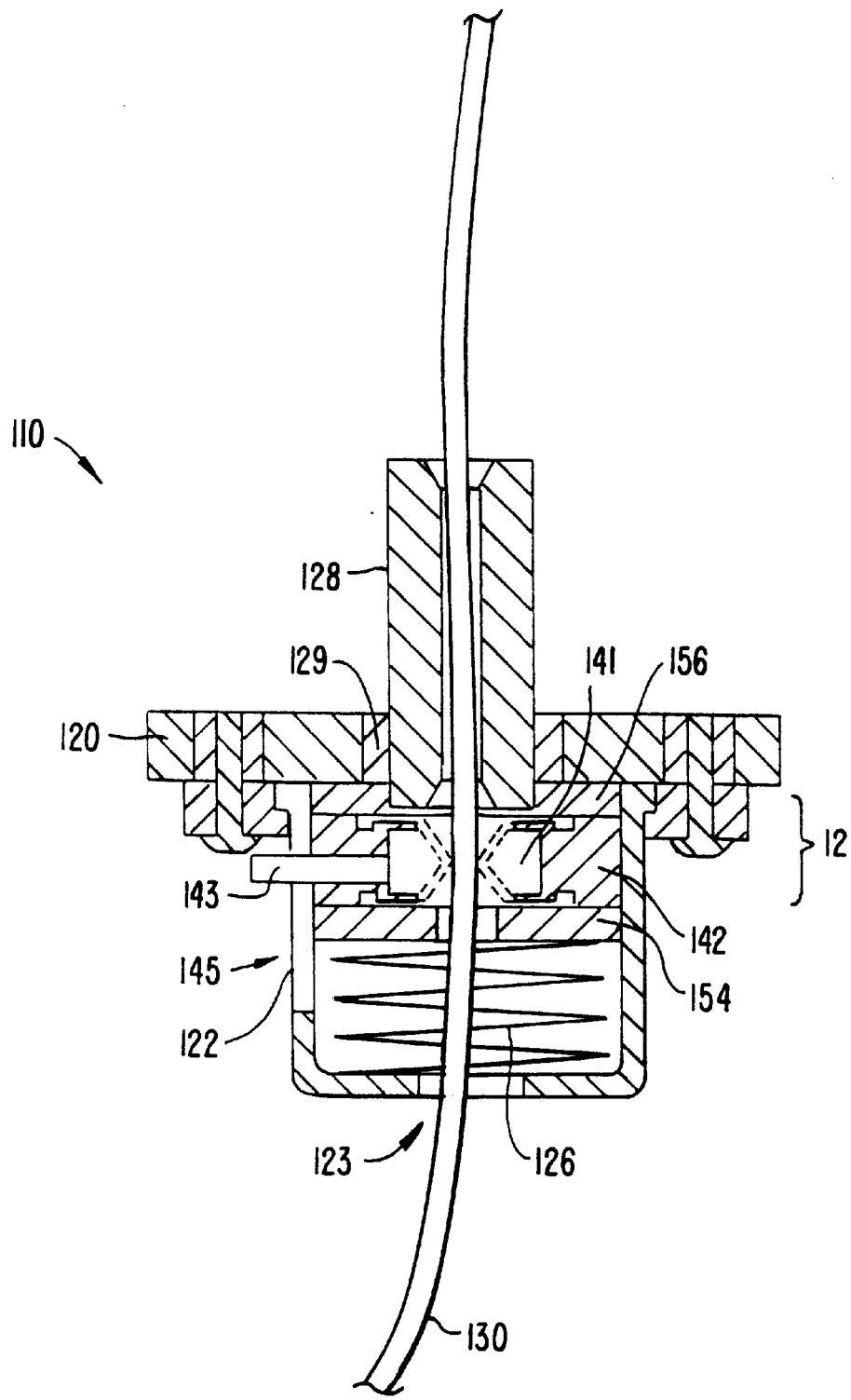
FIG. 7 is a view corresponding to FIG. 6F, but with a catheter received through the holder.

As shown in FIG. 7, catheter 130 is preferably received through an opening 123 in suspension housing 122 and passes longitudinally through catheter holder 110, as shown. Torroidal balloon 141 is inflated by way of pressure tube 143, which can be connected a pneumatic or a hydraulic pressure system (not shown). As torroidal balloon 141 is inflated, its center orifice will tend to close as the innermost sides of balloon 141 expand inwardly, thereby gently pushing radially inwardly upon the side of catheter 130 around its circumference, thus holding catheter 130 in a fixed position relative to balloon 141.

Catheter securement device 124, (comprising torroidal balloon 141, support mount 142, pressure tube 143, and catheter guide 128), is adapted to slide longitudinally within suspension housing 122. As can be seen in FIGS. 6 and 6C, a groove 145 running longitudinally through suspension housing 122 provides freedom of longitudinal movement for pressure tube 143, which passes therethrough, as shown.

In preferred aspects of the invention, torroidal balloon 141 is made of silicon rubber, and support housing 122 and catheter guide 128 are made either of aluminum, or a polycarbonate material. It is to be understood, however, that support housing 122 and catheter guide 128 can be made of any suitable bio-compatible material.

Further structural details of the present invention are seen in the exploded view of FIG. 6. A pair of fasteners 150 can be used to secure housing flange 152 to supporting base 120. Backing plates 154 and 156 can also be provided on opposite sides of catheter securement device 124. Backing plates 154 and 156 may preferably be made of aluminum. Fasteners 158 can be provided for securing backing plates 154 and 156 to catheter securement device 124.

Figure 12:
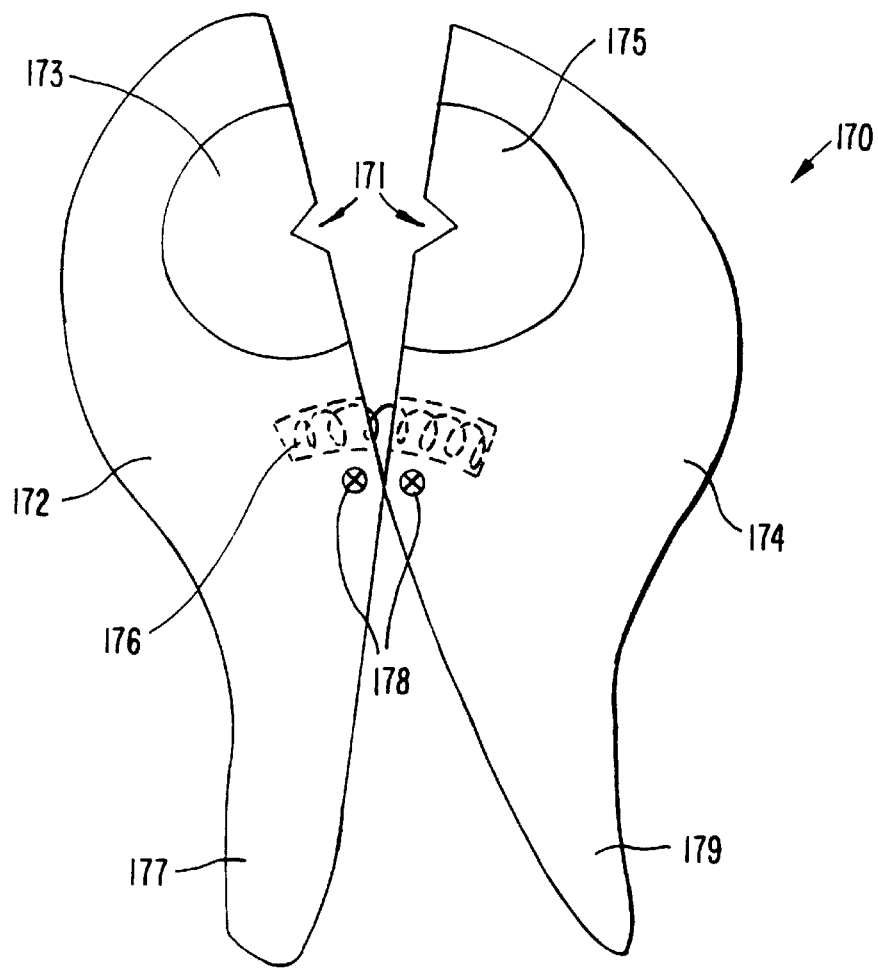
FIG. 12 shows a mechanical clamp for use in the catheter securement device.
Figure 13:
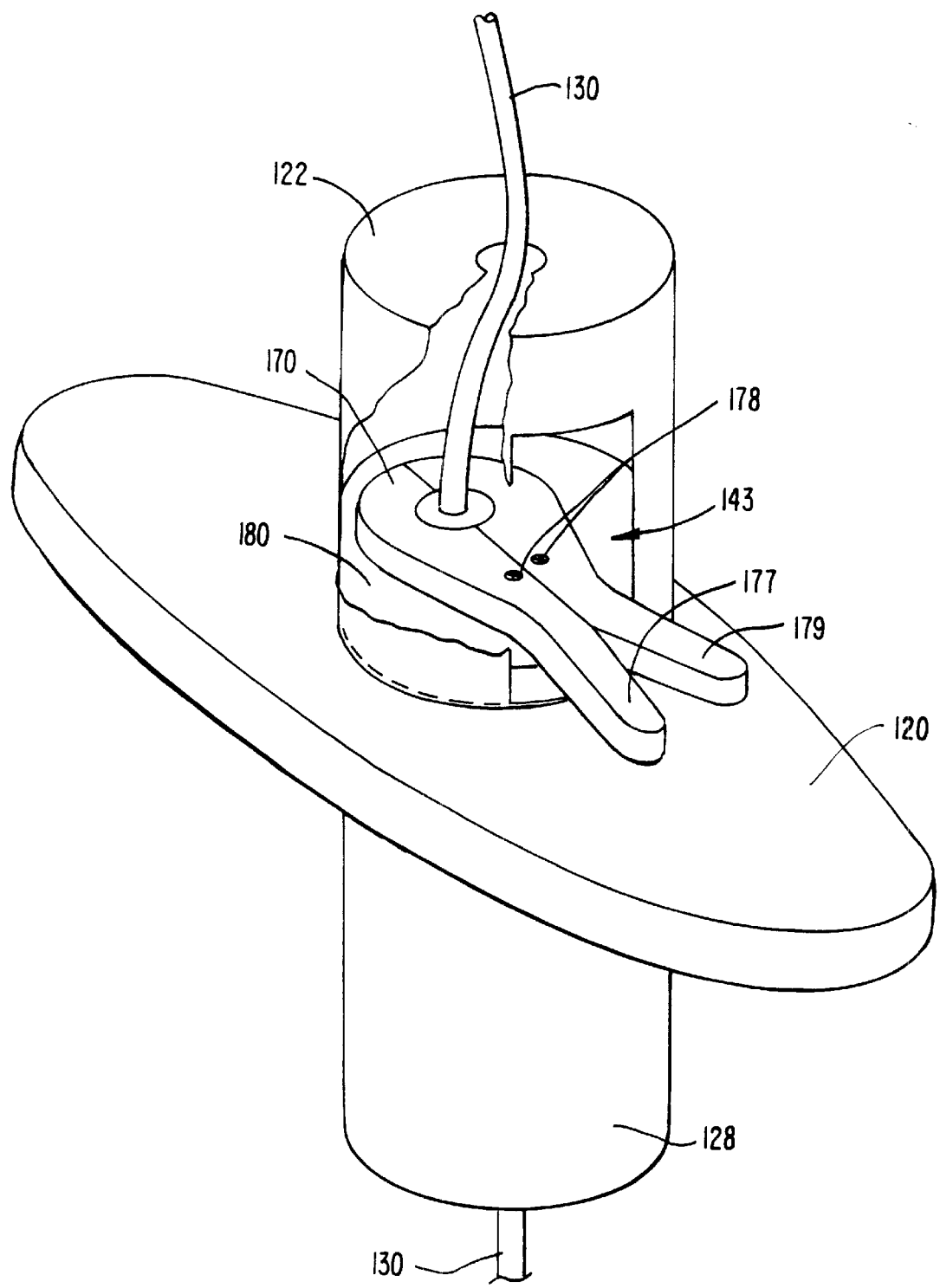
FIG. 13 shows a perspective view of an alternate embodiment of the present invention, comprising the mechanical clamp of FIG. 12.

An alternate embodiment of the catheter securement device is shown in FIGS. 12 and 13. The system shown in FIGS. 12 and 13 operates similar to catheter system 124, moving to track movement of the patient's urethra, as explained herein. Instead of using a torroidal balloon and balloon support mount, a mechanical clamping system which moves longitudinally in response to urethral movement is provided.

Referring to FIG. 12, a mechanical clamp 170 is provided. Clamp 170 comprises a pair of hard opposite portions 172 and 174 supporting soft inner surfaces 173 and 175 which may be manufactured of silicone or medical tubing. A notch 171 is provided for supporting a catheter therein as illustrated in FIG. 13. A spring 176 will bias hard opposite portions 172 and 174 together, closing clamp 170 around a catheter received therein. As seen in FIG. 13, clamp 170 can be mounted to a backing 180, wherein backing 180 moves longitudinally in suspension housing 122 under the influence of a biasing element, (functioning in the manner of biasing element 126 as herein described). As can be seen, levers 177 and 179 project out through groove 143. Pinching on levers 177 and 179 causes opposite portions 172 and 174 to separate, such that catheter 130 can be received therein. Levers 177 and 179 move longitudinally in groove 143 when catheter groove 128 and backing 180 move in response to movement of the patient's urethra. Clamp 170 may be secured to backing 180 by a pair of pins 178. It is to be understood that other mechanical clamping systems are possible, all keeping within the scope of the present invention, including the use of both expansion and compression springs to cause the mechanical clamp to securely hold the catheter in position.

Figure 8:
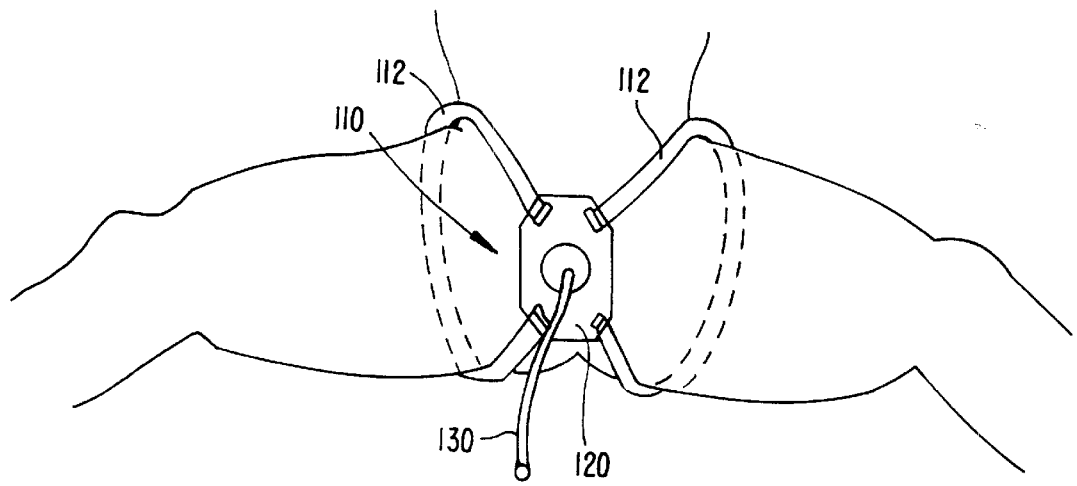
FIG. 8 shows positioning of the catheter holder by way of leg straps.
Figure 9:
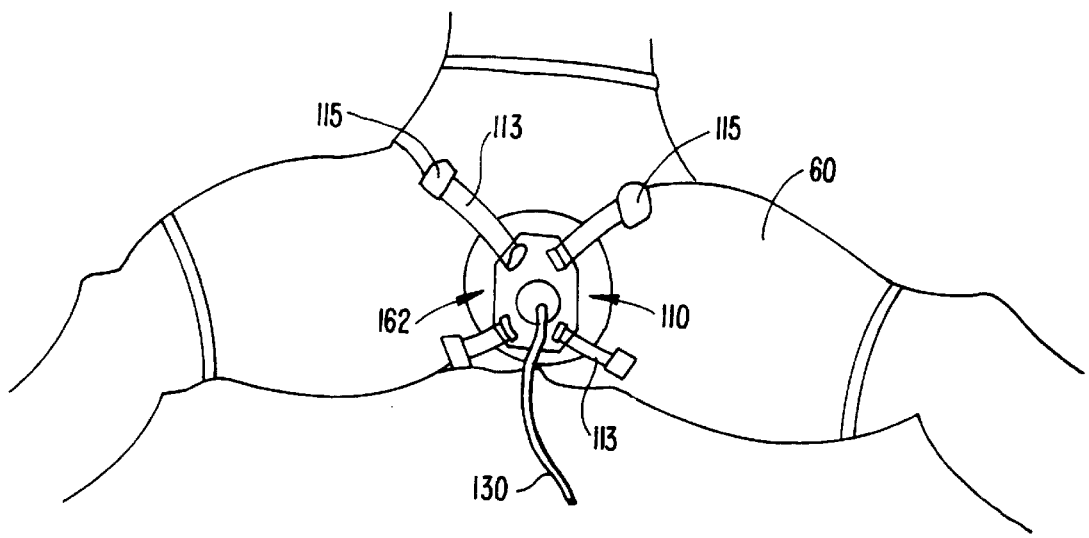
FIG. 9 shows positioning of the catheter holder by way of leg straps and a stretchable undergarment.

In a preferred aspect of the invention, optional leg straps are provided for registering the supporting base 120 of catheter holder 110 against the labia of the patient as catheter guide 128 moves with the urethra. Referring to FIG. 8, catheter holder 110 can be held in position with two leg straps 112 connected at opposite ends to supporting base 120, as shown. Alternatively, as shown in FIG. 9, a stretchable undergarment 160 can be worn by the patient. Undergarment 160 has an opening 162 over which catheter holder 110 can be fastened in position by way of four leg straps 113, wherein each of leg straps 113 have a Velcro-type patch 115 at their ends as shown for connecting fastening leg straps 113 directly to stretchable undergarment 160. Leg straps 112 may themselves be secured to slots 148 in supporting base 120 either by hooks (not shown) or by passing an end of each leg strap 112 through slot 160 and then folding the leg strap over upon itself and securing it into position with a Velcro-type fastener.

Figure 10:
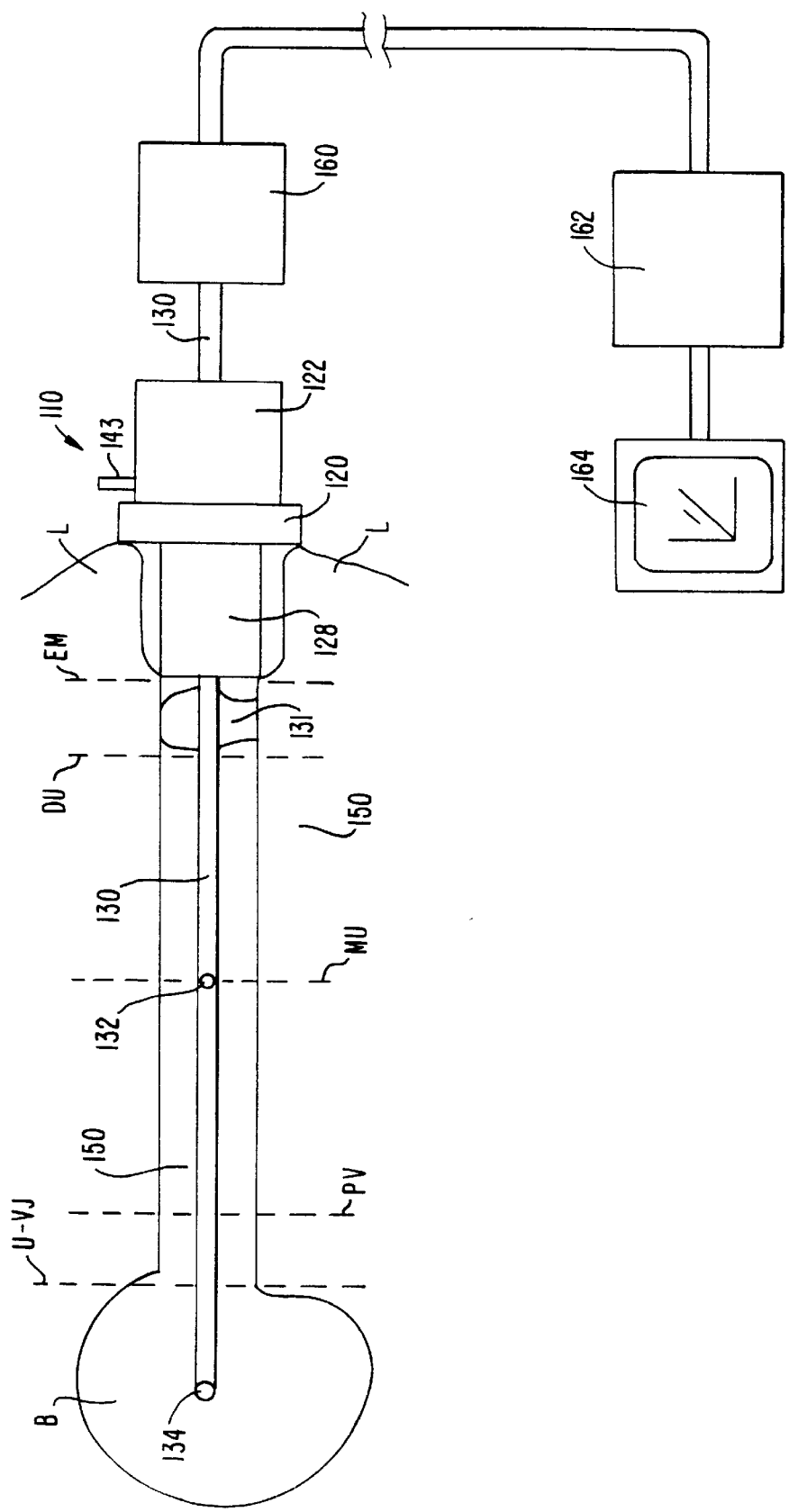
FIG. 10 is a schematic view of a system for evaluating female urinary incontinence incorporating the present urethral catheter holder.

In another aspect of the present invention, a system for evaluating female urinary incontinence is provided. Preferably, the system for evaluating female urinary incontinence comprises the present urethral catheter system as above described. Referring to FIG. 10, catheter 130 has pressure sensors 132, 134 disposed thereon, as shown. Catheter 130 is preferably inserted through urethra 150 into bladder B. Catheter 130 is then controllably retracted through urethra 150 by a mechanical retractor 160. Accordingly, pressure sensors 132, 134 can be positioned to take pressure measurements at each of the proximal urethra PU (which is located approximately 5–10 mm from the urethro-vesicle junction U-VJ), the mid-urethra MU, (where the vesicle pressure is greatest), to the distal urethra (which is located approximately 5–10 mm from the external meatus EM). It is to be understood that the present invention can operate with one or more pressure sensors 132, 134 since catheter 130 can be retracted through urethra 150. As can be seen, supporting plate 120 rests against the patient's labia L.

In a preferred aspect, an anchoring structure for catheter 130 can comprise a catheter positioning surface 131, such as an expandable balloon positioned between the patient's distal urethra DU and external meatus EM to engage soft tissues of urethra 150 so as to inhibit movement of catheter 130 within urethra 150 when the patent coughs. Alternatively, the outer surface of catheter 130 can be textured so as to gently grip against the sides of urethra 150, thereby holding catheter 130 in a fixed relative position to urethra 150. In a preferred aspect, a removable sheath is preferably received over the high friction surface such that the catheter can be conveniently inserted into the patient and positioned at a desired location. The sheath is then removed, such that the high friction surface of the catheter engages the walls of the urethra. Alternatively, fluid may be injected into the urethra, causing it to expand while the high friction surface catheter is inserted. Removal of the fluid surrounding the catheter will cause the urethra to collapse inwardly, such that the high friction surface of the catheter engages the walls of the urethra.

Measuring the patient's vesicle and urethral pressures with a pressure-sensing catheter can be accomplished by first moving a pressure sensor on the catheter from the patient's bladder, (at which the vesicle pressure is measured), through the patient's urethra (at which maximum urethral pressure is measured) to determine the maximum urethral pressure, as described above. A urinary catheter with internal or external pressure transducers can be used to take pressure measurements at the proximal urethra, mid-urethra, and/or distal urethra. Typically, such a pressure-sensing catheter is first introduced through the urethra into the bladder. The pressure-sensing catheter is then withdrawn through the urethra with pressure measurements taken at the proximal urethra (being 5–10 mm from the urethro-vesicle junction), the mid-urethra (being the point of maximum resting urethral pressure) and the distal urethra, (being 5–10 mm from the external meatus). For generating a pressuregram, the urethral pressure sensor will generally be positioned at the maximum pressure location, often called the mid-urethra, as described above.

Abdominal pressure transients or pulses can conveniently be generated simply by having the patient cough with different amounts of effort. For example, a mild couch would generate a minimal increase in abdominal pressure, whereas a more intense cough will generate a greater abdominal pressure. The increase in abdominal pressure will cause both the urethral pressure (including the maximum urethral pressure) and the vesicle pressures to increase. A continence margin can be defined by the difference between the patient's maximum urethral pressure and the vesicle pressure.

Figure 11:
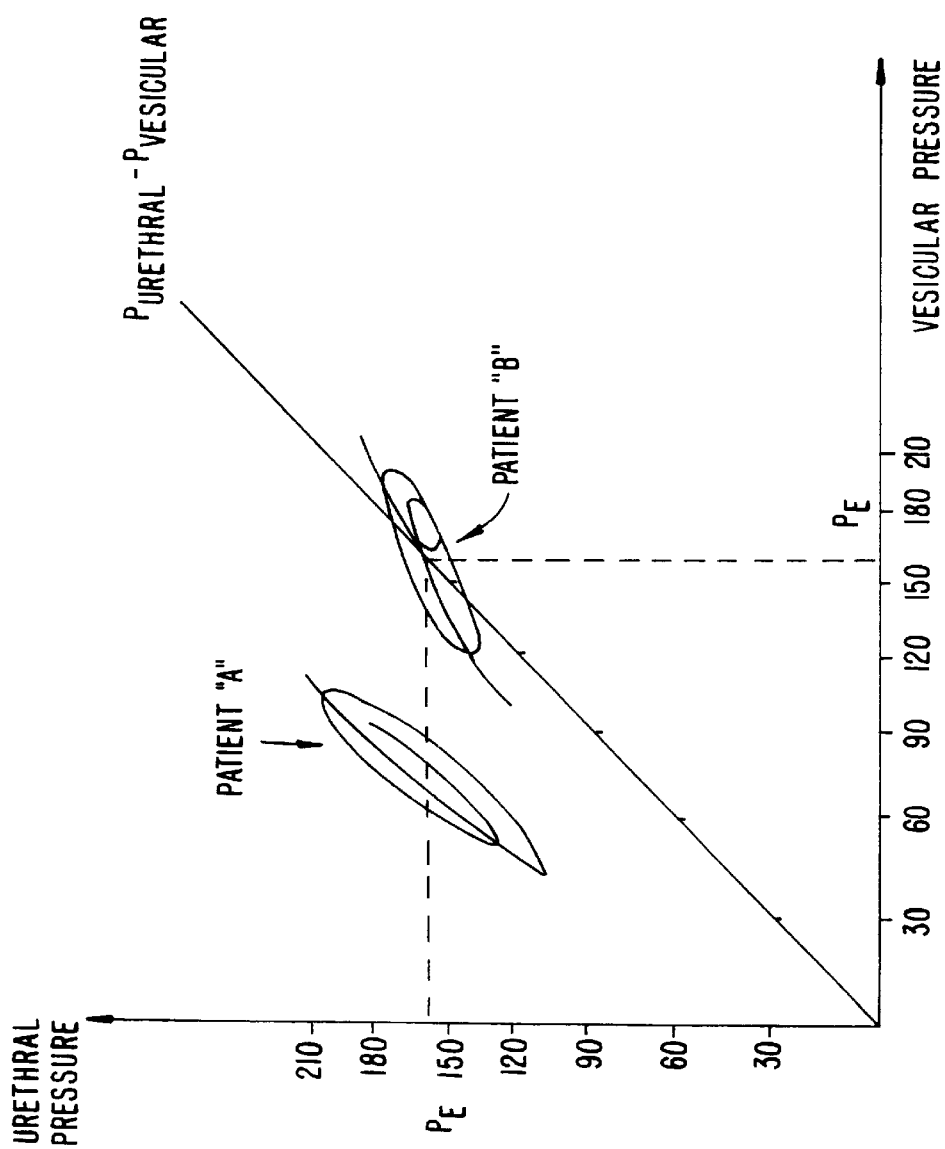
FIG. 11 is an illustration of a pressuregram showing the relationship between the vesicle pressure and the urethral pressure for two different patients at different abdominal pressures.

The pressures measured by pressure sensor 130 are received by computer system 162 and are displayed as a pressuregram on display terminal 164. FIG. 11 shows an exemplary pressuregram in which urethral pressure is plotted against vesicle pressure. The pressuregram shows the relationship between urethral and vesicle pressure for two different patients for different abdominal pressures caused by the patient coughing. Patient A's urethral pressure always exceeds her vesicle pressure, therefore patient A remains continent. For patient "B", however, her urethral pressure may be above or below her vesicle pressure, (as signified by her pressure data dropping below line $P_{urethral}=P_{vesicle}$), thus indicating incontinence at certain abdominal pressures. More specifically, above an equilibrium pressure Pe, leakage of urine will likely occur.

Figure 14:
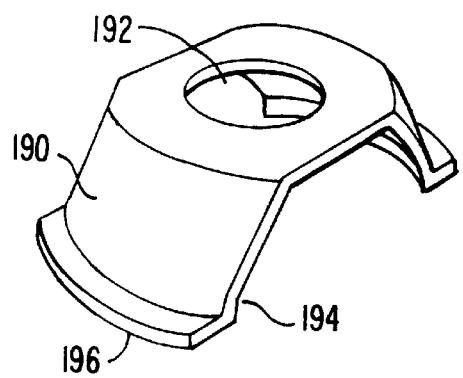
FIG. 14 illustrates an alternative anchoring surface for engaging a tissue adjacent the urethral opening and for allowing the system operator to visually monitor for leakage.

Referring now to FIG. 14, a tissue engaging structure 190 includes a central passage 192 for receiving the catheter, and side cutouts 194 which define channels when a positioning surface 196 of the tissue engaging structure engages the soft tissues adjacent the external meatus. These channels allow a system operator to observe when leakage occurs during pressuregram testing, and may also allow observation of the urethra. Tissue engaging structure 190 may be fabricated from a transparent polymer material to further minimize any obstruction of the physician's view, and such tissue engaging structures may be incorporated into many of the anchoring structures described above.

Figure 15A:
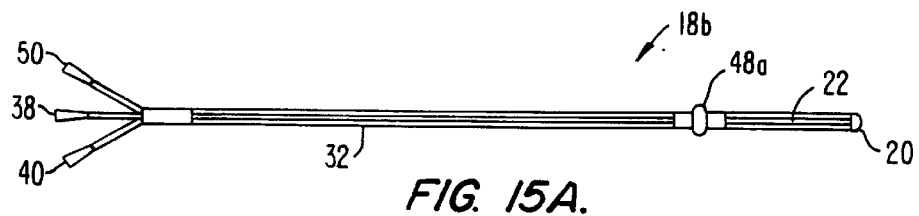
FIGS. 15A and 15B schematically illustrate a pressure measurement catheter anchored within the urethra by a multiple-lobed balloon, the balloon defining axial passages when inflated within a urethra so as to decrease pressure effects of the measurement system.
Figure 15B:
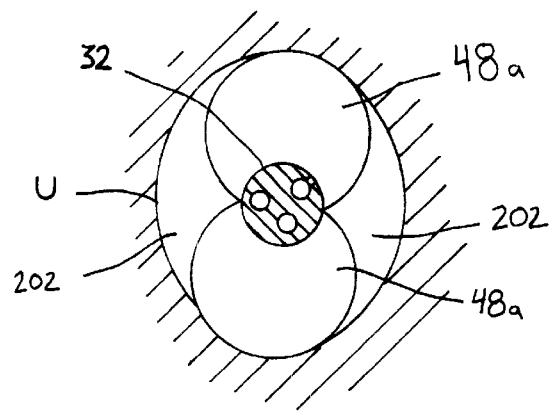

A still further alternative pressure sensing catheter 18b is illustrated in FIGS. 15A and 15B, here having a two-lobed balloon 48a which defines channels when inflated within urethra U. Hence, the tissue engaging and positioning surface of the anchoring structure may optionally engage the tissue along the urethra.

Figure 16:
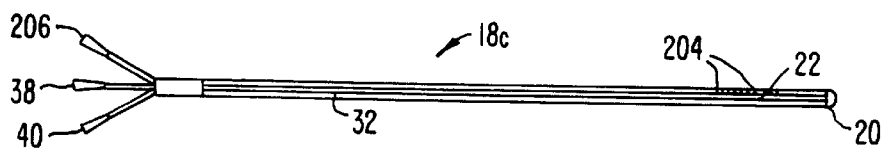
FIG. 16 illustrates an alternative pressure measurement catheter which can be anchored within the urethra by a series of vacuum ports on a surface of the catheter.

Referring now to FIG. 16, a vacuum secured pressure sensing catheter 18c includes at least one (and preferably an array of) vacuum port 204. The vacuum port array will preferably comprise between about 12 and 30 small openings, each typically having a diameter in a range from about 0.010 inches to about 0.040 inches. Vacuum ports 204 will preferably open to a common lumen of catheter body 32 for coupling to an external vacuum source via a vacuum connector 206, although two or more vacuum lumens could alternatively be used. In the exemplary embodiment, two linear arrays of 10 ports each are offset by about 90 degrees about the axis of the catheter body, thereby defining 10 pairs of ports. The vacuum ports are disposed within 5 cm proximally and/or distally of urethral pressure sensor 22 so that the ports can engage the tissue along the urethra when the urethral pressure sensor is disposed at the target maximum urethral pressure location.

In use, vacuum catheter 18c will be inserted into the urethra while the vacuum ports are inactive. Once urethral pressure sensor is axially positioned at the maximum urethral pressure location, vacuum ports 204 are activated, securing the catheter body around the ports into fixed engagement with the urethral wall along the urethra. As no anchoring structure protrudes from catheter body 32, flow-induced changes in pressures during urodynamic testing may be avoided.

Figure 17:
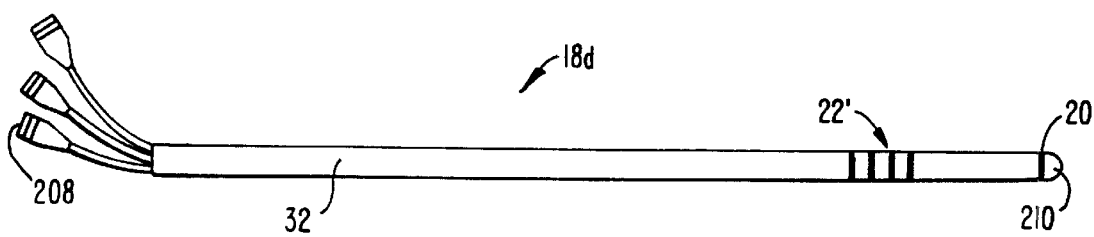
FIG. 17 illustrates an alternative pressure measurement catheter having a plurality of independent axially separated urethral pressure sensors so as to decrease sensitivity of the pressure sensor system to movement between the catheter and maximum urethral pressure.

Yet another alternative pressure sensing catheter 18d is illustrated in FIG. 17. Here, an array of urethral pressure sensors 22' include a series of individual pressure sensors which are axially distributed along catheter body 32.

Preferably, the individual pressure sensors are separated by less than 10 mm, and ideally by less than 5 mm so as to allow at least one of the pressure sensors to accurately approximate the peak urethral pressure whenever the maximum pressure is disposed along the array. As described above, the individual pressure sensors may comprise piezo-electric transducers carried by the catheter body, optical pressure sensors, fluid ports fluidly coupled to external transducers, or the like. Array of transducers 22' thereby reduces the sensitivity of the pressure sensing system to positioning of the catheter, allowing the processor to select a maximum urethral pressure even if the catheter moves during testing, and also giving a broader range for placement of the catheter. As was also described above, a fluid fill coupler 208 allows fluid to be introduced into the bladder via a bladder fill port 210 prior to testing.

Sample data and pressuregrams are illustrated in FIGS. 18–22. The dataset of FIG. 18 illustrates maximum urethral and vesicle pressures taken substantially simultaneously at sampling intervals and transmitted by the pressure sensing system to the processor, and may also show abdominal pressure. The processor stores the sampled pressures and also plots the pressuregram in real time, for example, while the test is underway and the catheter remains affixed in position. Multiple pressure pulse plots can be superimposed on the display to illustrate the repeatability of the measurements. The operator has the option of refreshing the screen as desired to view results in isolation.

Figure 19:
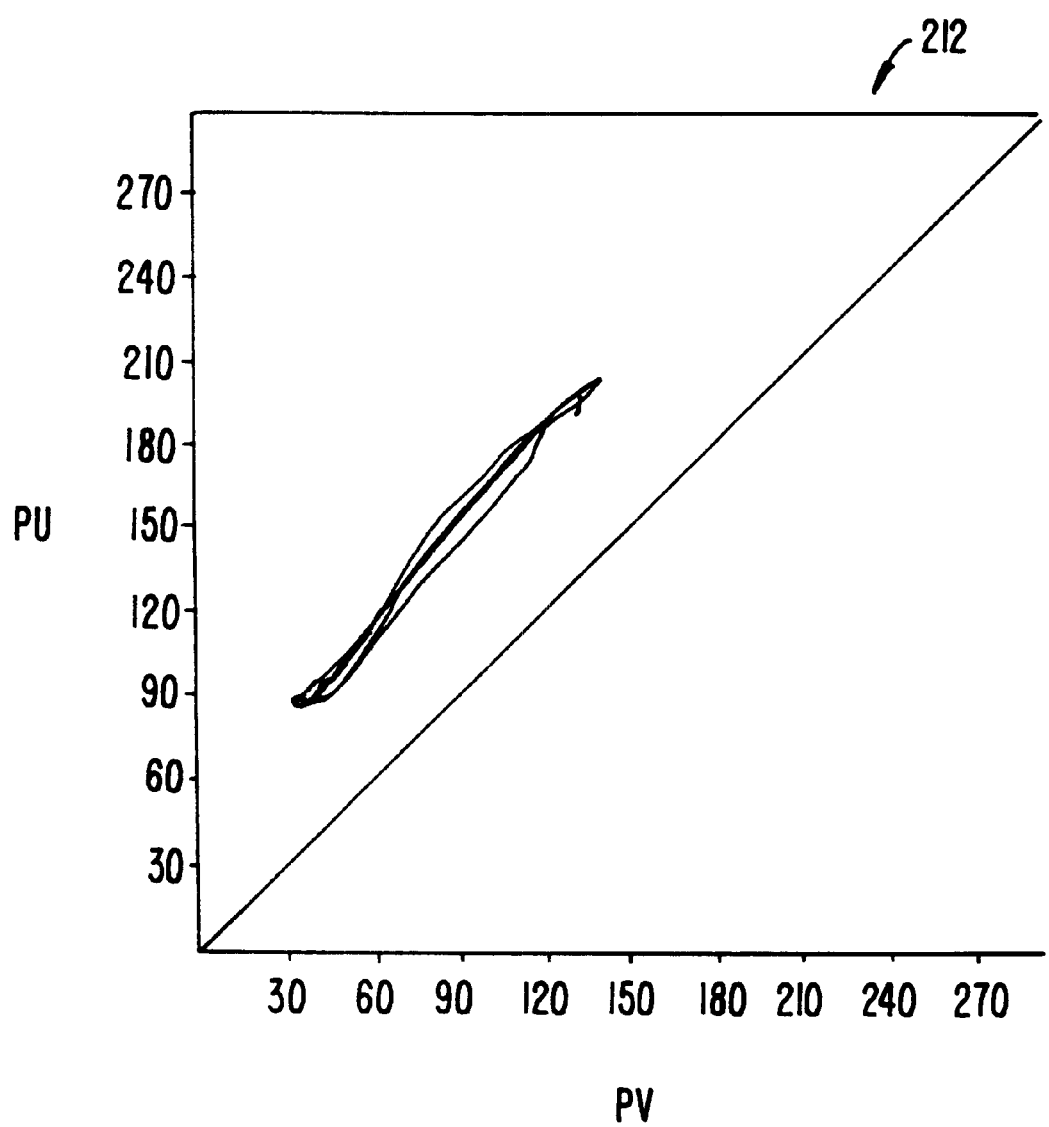
FIG. 19 is a pressuregram of a continent woman taken with minimal relative movement between the measurement catheter and the urethra.
Figure 20A:
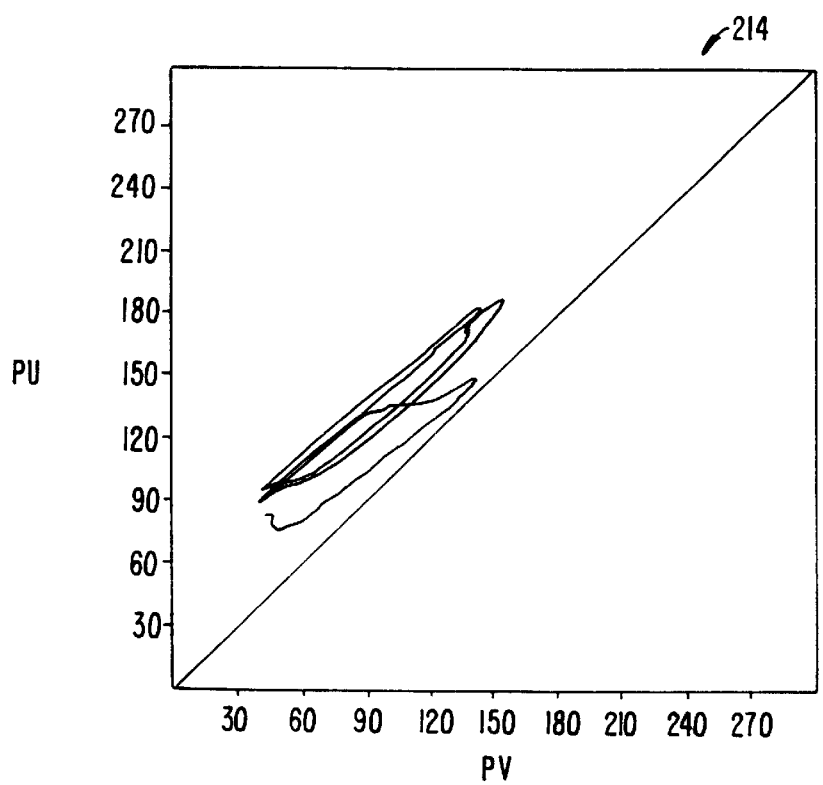
FIGS. 20A and 20B are pressuregrams taken with significant relative movement between the measurement catheter and the urethra.
Figure 20B:
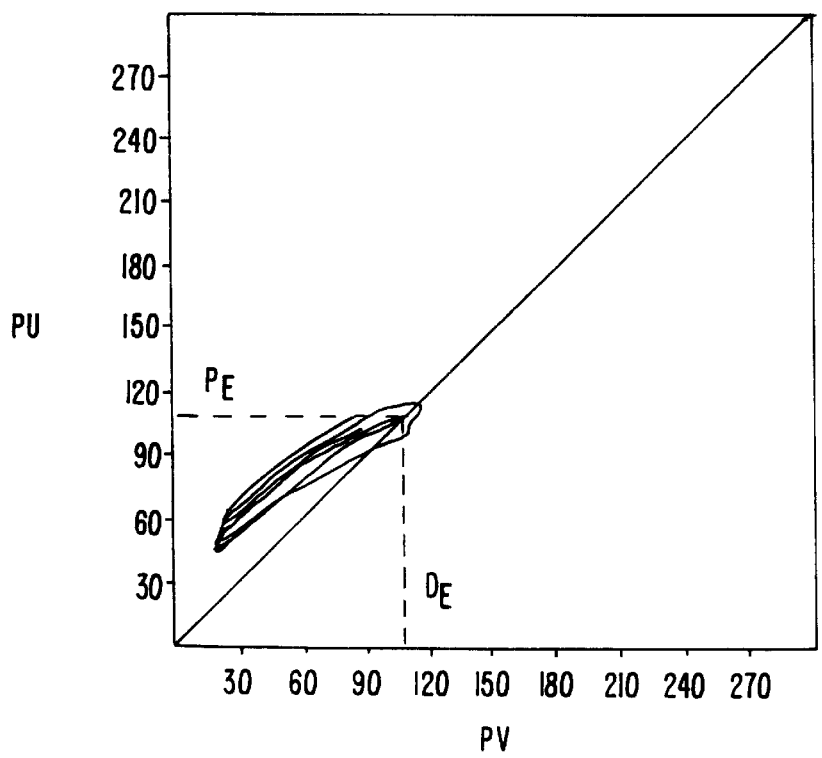

Pressuregram 212 illustrated in FIG. 19 was taken with the patient in a sitting position, and shows a plot representative of a continent woman. As PU appears to rise faster than PV during the pressure pulse, there does not appear to be any point at which a pulse will lead to a leakage event. As little or no catheter movement occurred during this test taken in a sitting position, results remain repeatable throughout three separate pressure pulses induced by three hard coughs. In contrast, pressuregram 214 of FIG. 20A, which was taken with the patient in a standing position, illustrates how results can be altered by movement of the catheter. As the results here appear inconsistent, the test can be rerun. Catheter movement can also produce apparently consistent results, as can be understood with reference to FIG. 20B, which appears to show the vesicle pressure will exceed the urethral pressure above the equilibrium pressure Pe. The processor can calculate Pe by extrapolating a curve-fit approximation of the pressuregram plot. Despite the apparent exceeding of the equivalence pressure, no leakage was observed. The catheter anchoring structure described above can substantially improve reliability of these pressuregram plots.

Figure 23A:
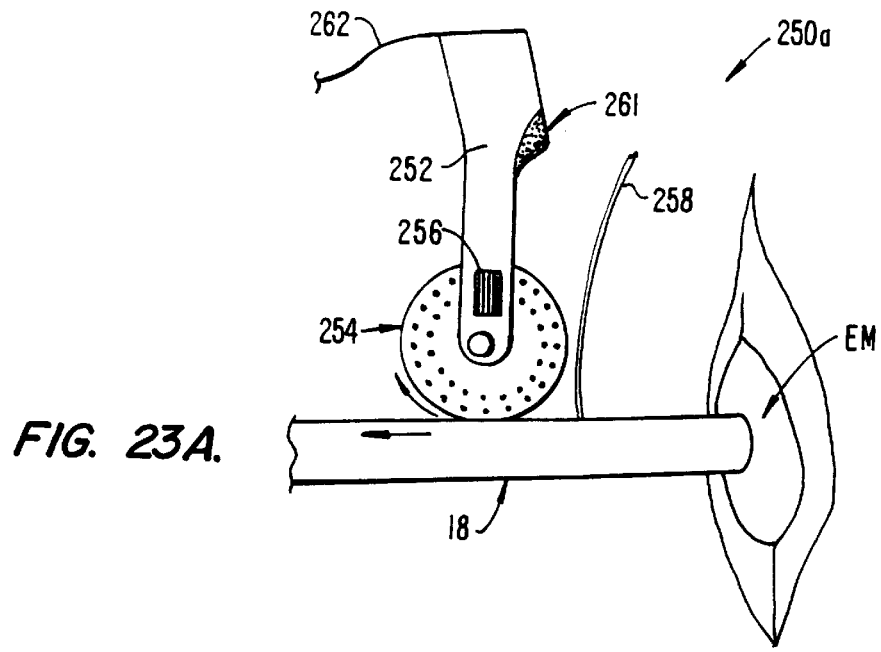
FIGS. 23A–C schematically illustrate devices and methods for measuring a urethral pressure profile as illustrated in FIG. 3B, in which the profile accuracy can be independent of the rate at which the pressure sensor moves.
Figure 23B:
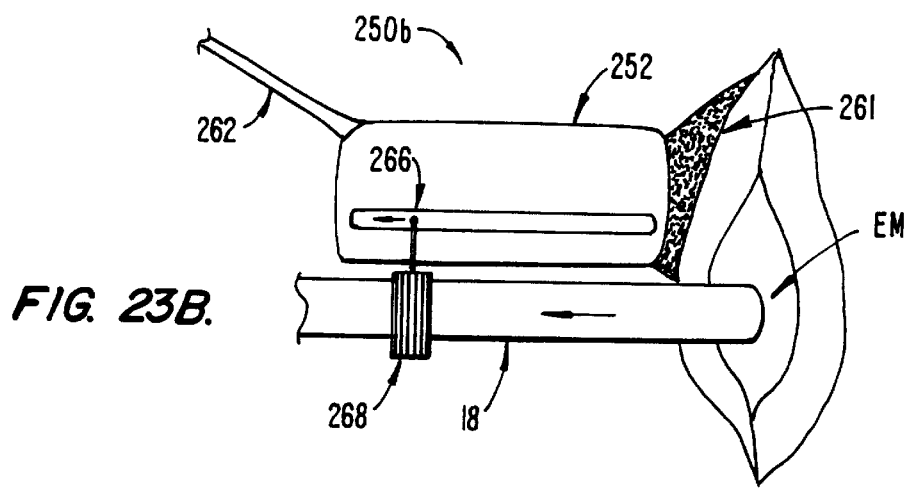
Figure 23C:
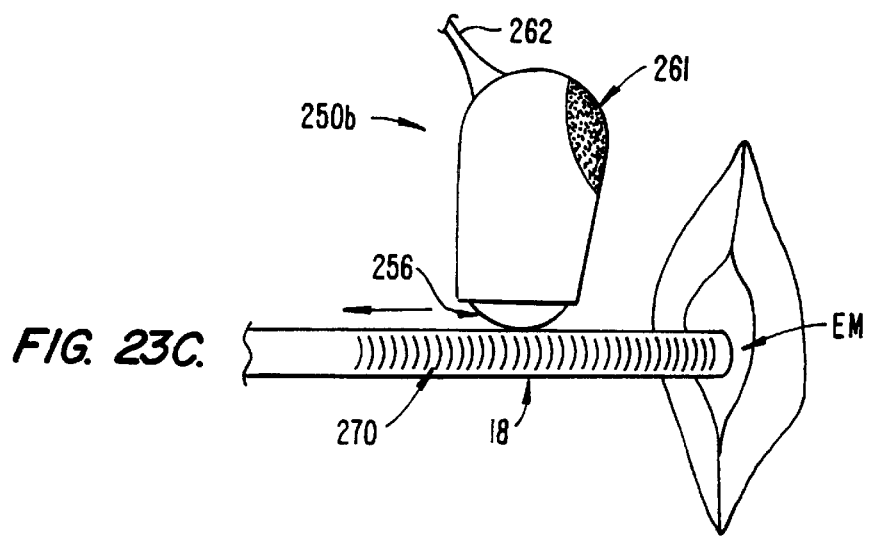

Referring now to FIGS. 23A–C, the invention also provides pressure profile systems 250*a*, 250*b*, and 250*c* (collectively referred to as pressure profile systems 250) including axial position sensors so that the system can accurately measure and plot urethral pressure along the length of urethra U. Rather than attempting to translate a urethral pressure sensor along the urethra at a constant rate, pressure profile systems 250 provide axial pressure sensor position measurements in correlation with pressure measurements from the urethral pressure sensor. These associated position and pressure measurements allow an accurate pressure plot of pressures along the length of the urethra to be generated regardless of variations in the rate of movement of the sensor, as the plotted data can be independent of the measurement time.

An optical encoder position sensing system 250*a* is schematically shown in FIG. 23A. A housing 252 rotatably supports a pickup wheel 254 in rolling engagement with catheter 18. An optical pickup 256 is also mounted to housing 252, and the housing may be supported in a fixed position by engagement between a surface 260 of the housing and a tissue such as thigh 258 or the like (see FIG. 23B), by coupling the housing to an anchoring structure axially affixed relative to the urethra as described above, by independently supporting the housing, or the like. If an anchoring structure of the pressure sensing system is used to support the housing, the anchoring structure will often be capable of allowing axial movement of the catheter, as was described above.

When catheter 18 is moved proximally, whether manually or with an automated puller mechanism, a switch 261 can be actuated so that the processor measures axial movement of catheter in correlation with the pressure measurements from the urethral pressure sensor of the catheter. More specifically, pickup 256 transmits signal via cable to processor 14 in response to rotation of wheel 254, and the processor determines and stores an axial position of catheter 18 and/or pressure sensor 22 during pressure measurements using the signals from position sensing system 252.

FIGS. 23B and 23C illustrate alternative position sensors of related pressure profile systems. In a linear position sensor 250*b*, a linear sensor such a linear potentiometer 266 is actuated by movement of catheter 18. Catheter 18 may be coupled to the wiper of potentiometer 266 by a quick release clamp 268, thereby providing an absolute analog position signal to processor 14. Direct optical position sensor 250*b* includes an optical pickup which directly reads optical measurement indicators 270 of catheter 18, the indicators being similar to bar codes. Catheter 18 will typically include regularly spaced markers for visual reference by the system operator, and indicators 270 may be incorporated into these markers. Regardless of the specific positioning system, the signal will preferably indicate the direction (distal or proximal) and amount of catheter travel, permitting the operator to concentrate on manipulation of the catheter instead of data system operation.

Figure 21:
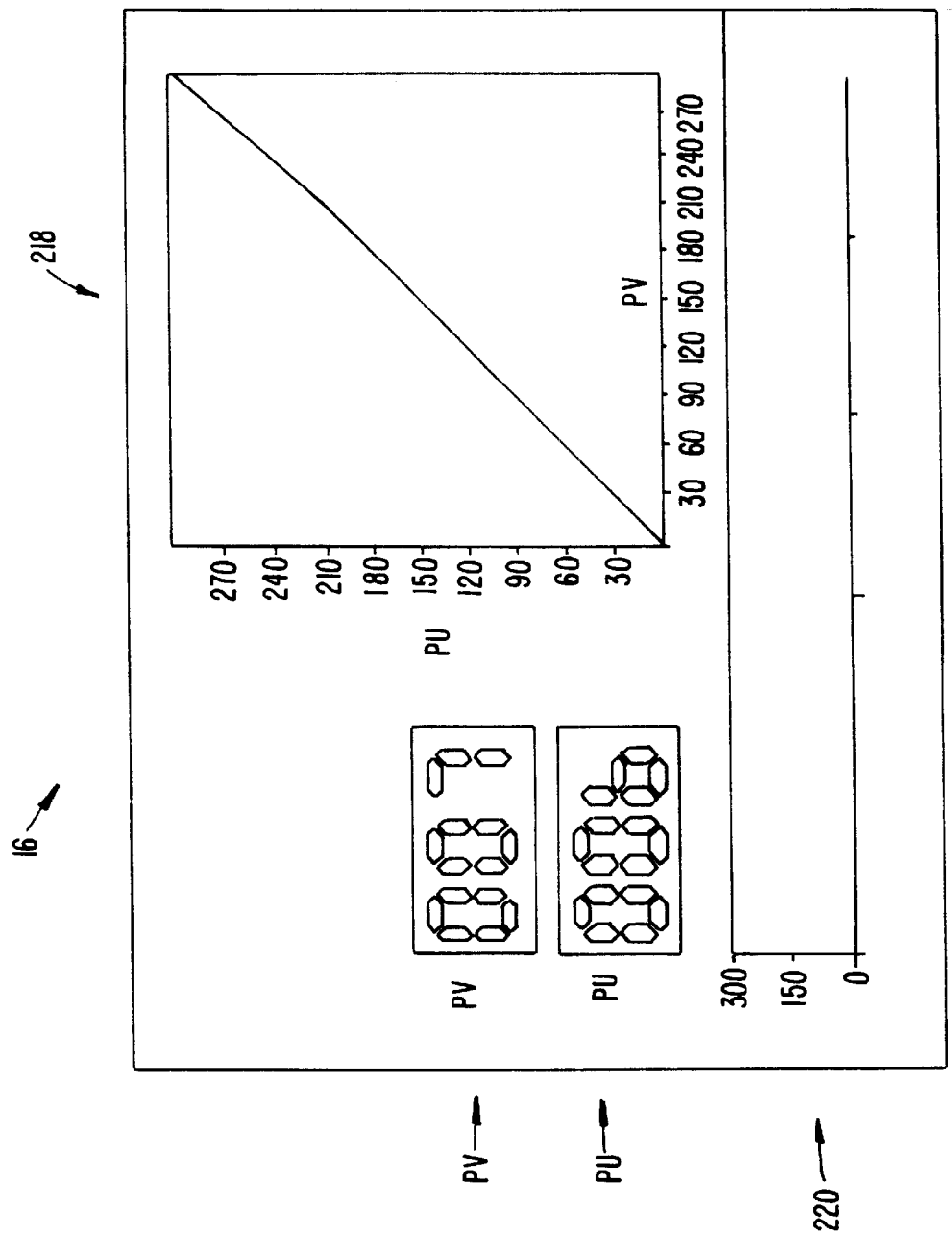
FIG. 21 schematically illustrates a screen displaying a real-time pressuregram to a pressuregram system operator.

FIG. 21 shows an arrangement of information which may be included in display 16 to facilitate incontinence diagnosis using the system of FIG. 1. Along with pressuregram 218, PV, and particularly, PU are shown in real time so that the operator can use display 16 to help position the urethral sensor at the location of maximum urethral pressure, the pressures preferably being sufficiently large to be read by persons of average visual acuity at a distance of at least 8 feet. Optionally, a pressure plot 220 of PU and/or PV (and in many cases, abdominal pressure PA) will often be taken and plotted throughout a sampling time, that is, as pressure verses time. Alternatively, using the devices of FIGS. 23A–C, pressure plot 220 may show PU and/or PV plotted against an axial distance, such as along the length of urethra U.

Figure 22:
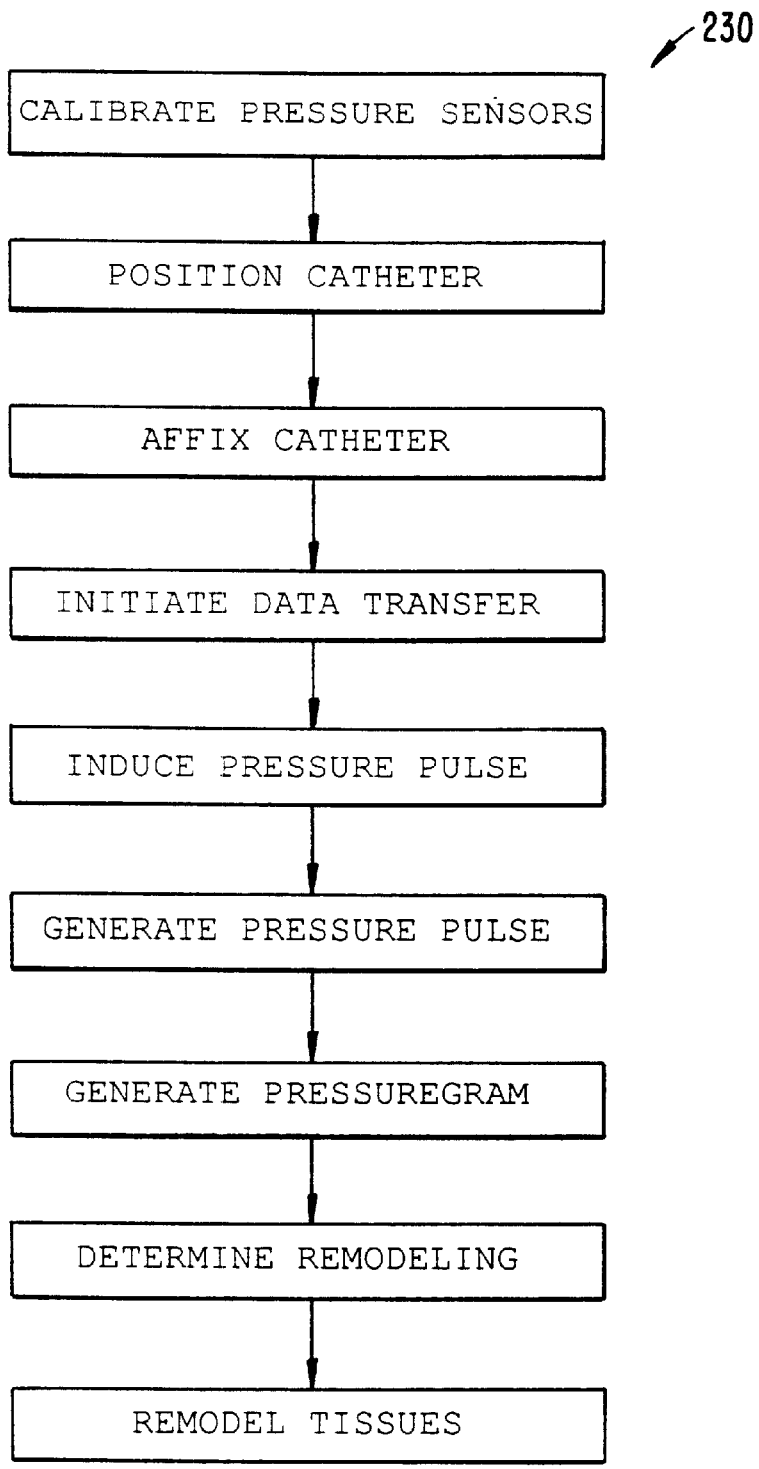
FIG. 22 is a flow chart showing exemplary method steps for diagnosing and/or treating urinary incontinence.

FIG. 22 schematically illustrates a method 230 for diagnosing and treating a patient using the diagnostic systems described above. The urethral and vesicle pressure sensors will be calibrated, and if appropriate, some or all of the pressure sensing system may be sterilized prior to testing. The pressure sensing catheter is positioned, preferably with reference to the display showing urethral pressure PU, so that the urethral pressure sensor is aligned with the location of the maximum urethral pressure when the patient is at rest, and so that the vesicle pressure sensor is exposed to bladder pressure. The pressure sensors may also be rotationally positioned by rotating catheter 18. The aligned catheter is held in position using any of the anchoring structures described above. Data transfer, storage, and/or display is initiated, and a pressure pulse is initiated, typically by having the patient cough. At least one pressuregram is generated from the urethral and vesicle pressure during the pressure pulse.

In many cases, it will be advantageous to generate a plurality of pressuregrams with pressure pulses of varying intensities, and/or with the patient in a variety of positions, such as standing, sitting, supine, and the like. Using the pressuregram, a desired remodeling of the pelvic support tissues can be determined so as to inhibit incontinence. The desired remodeling may then be performed as described below.

The present invention also provides methods, devices, and systems which enhance the structural support provided by a body's tissues, particularly as a therapy for incontinence. The techniques of the invention will generally involve contraction of tissue, promoting the formation of scar tissue so as to stiffen a tissue structure, and/or the attachment of two adjacent tissues (which are normally free to slide relative to each other) to each other. Energy may be directed from a probe into one or more fascial tissues of the pelvic support system. The energy may lead to the formation of stiff scar tissue, and/or it may attach adjacent fascial tissues together by fusing, cross-linking of collagen, the formation of adhesions, or the like. Optionally, the energy may also cause contraction of the fascial tissue by heating this collagenous layer to a contraction temperature over about 60° C. Alternatively, stiffening and/or attachment of adjacent fascial layers may be provided without significant contraction, as scar tissue can be promoted by heating the fascia to temperature below that at which significant contraction takes place, for example, over about 45° C.

The techniques of the present invention will often be used to stiffen or attach fascia, tendons, and other collagenous tissues, preferably without ablation of these collagenous tissues. As used herein, this means that collagenous tissues are not removed and their function (particularly their structural support function) is not destroyed. Histologically, some tissue necrosis may occur, and the structural strength of the tissues may initially decrease immediately after treatment. Nonetheless, the treated tissues will generally continue to provide at least some structural support, and their structural strength should increase during the healing process so that the healed tissue has preferably the same ultimate structural strength as, and often greater stiffness (for example, having a lower modulus of elasticity so as to stretch less under tension) than before treatment.

The hammock-like endopelvic fascia described above may be damaged or missing, particularly after pregnancy, so that the support of the genitourinary tract is instead provided by a variety of fascial layers, muscular tissues, ligaments, and/or tendons within the pelvis. Hence, the treatment of the present invention may be directed at a variety of tissue structures defining the pelvic floor and/or diaphragm (including: anterior sacro-coccygeal ligament; arcus tendineus fasciae pelvis (ATFP), the white line of the pelvis; fasciae of the obturator internus muscle; the arcus tendineus levator ani or "picket fence" to the iliococcygeus portion of the levator ani muscle; bulbocavemosus muscle; ischiocavemosus muscle; urethrovaginal sphincter; m. compressor urethrae muscle; and m. sphincter urethrovaginal muscle which replaces deep perineal muscle); structures of the bladder and urethra (including: urethrovesical fascia; detrusor muscle; and the pubococcygeus muscle which relaxes to open the bladder neck, initiating micturation); structures of the vagina (including: vagino-uterine fascia, lamina propria- the dense connective tissue layer just under the epithelium; pubo-urethral or puboprostatic ligaments; pubo-vesicle ligament and posterior pubo-urethral or pubo-prostatic ligament; pubovesicle muscle, a smooth muscle that is integrated with the pubo-vesicle ligament; and pubocervical fascia which attaches to the ATFP); structures of the uterus (including: round ligament; sacrouterine ligament; and broad ligament); and structures of the bowel (including: rectal fascia and Mackenrodt's ligament).

Figure 24B:
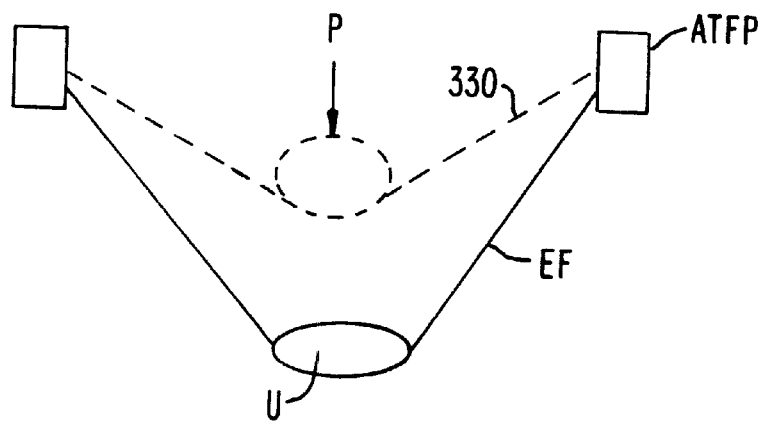
FIGS. 24A–C schematically illustrate methods for inhibiting incontinence by remodeling collagenous support tissues by transmitting energy to the tissues.
Figure 24C:
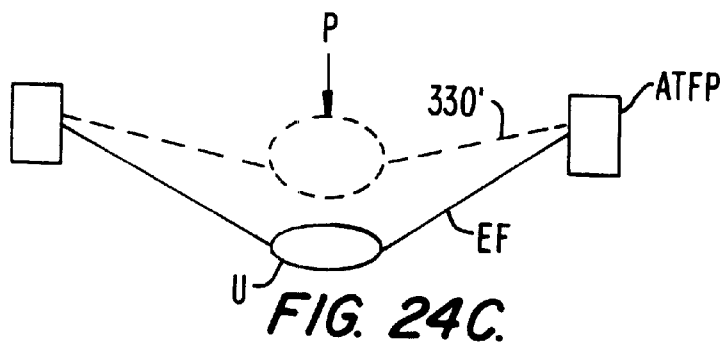
Figure 24A:
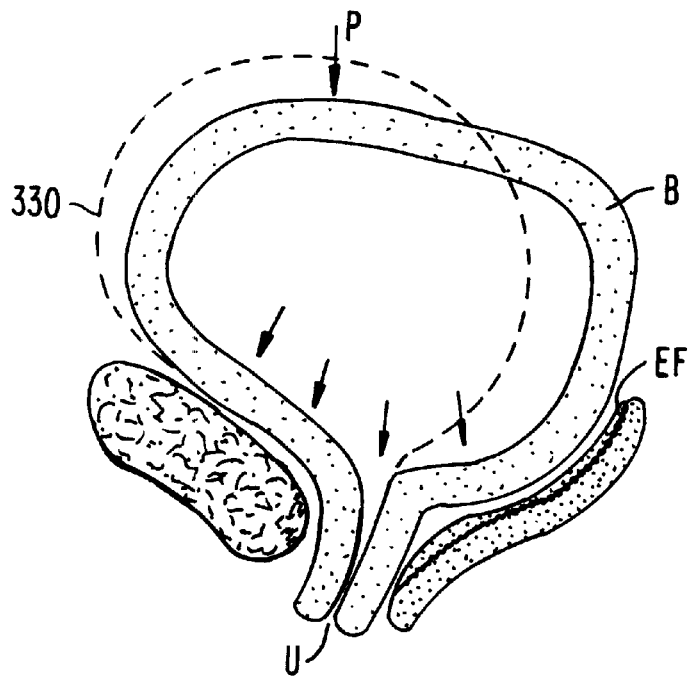

The effects of excessive elasticity of the pelvic support tissues are illustrated in FIGS. 24A–C. In FIG. 24A, a pressure pulse P moves bladder B from an initial position 330 to a lowered position as shown. As endopelvic fascia EF stretches excessively in this case, the fluid pressure within the bladder advances into the bladder neck and down urethra U. Leakage may result in part because the endopelvic fascia allows the bladder to drop below its initial position, at which fluid pressure within the bladder actually helps to seal the bladder neck. Perhaps even more importantly, stretching of the endopelvic fascia may alter the timing of pressure pulse transmission to urethra U.

When a continent woman coughs, the pressure in the urethra will often increase more than one-tenth of a second prior to the increase in bladder pressure. In women with stress incontinence, the bladder pressure may rise first. The effect of a stretched endopelvic fascia on this difference in timing can be understood with reference to FIGS. 24B and C.

FIG. 24B schematically illustrates a simplified theoretical pelvic support system for a woman with stress incontinence. When pressure pulse P first begins to act on urethra U, the bladder, bladder neck, and urethra are disposed at initial position 330. As endopelvic fascia stretches significantly under the effects of pressure pulse P, there is a significant time delay between initiation of the pressure pulse and transmission of a closing force against urethra U. For example, urethra U may be closed by transmission of pressure pulse P between one-tenth and one-half second after pulse is imposed on the bladder. Hence, leakage would occur during this time delay.

This situation is different for a continent woman having the simplified theoretical pelvic support system illustrated in FIG. 24C. In this case, endopelvic fascia EF stretches much less under the influence of pressure pulse P, so that the time delay between initiation of the pressure pulse and transferring sufficient force to urethra U to effect closure is significantly less. More specifically, an increase in the modulus of elasticity of the endopelvic fascia and the pelvic support system shortens the response time of the tissue system to momentary stress. By treating the endopelvic fascia to increase its stiffness, the decent time of the pelvic viscera during a cough will be much shorter than an untreated, highly elastic tissue.

It should be noted that the continent woman's support structure schematically illustrated in FIG. 24C has an initial position 330' in which the endopelvic fascia EF is more taut than the incontinent woman's structure illustrated in FIG. 24B. In other words, excessive length of the pelvic support tissues may add to the delay and bladder movement, independently of the effects of excessive elasticity. Hence, in many cases, it will be beneficial to both increase the modulus of the endopelvic fascia and decrease its length so as to improve continence. Advantageously, the collagenous fascial tissues may be selectively contracted using many of the same system components described herein, often by heating this collagenous tissue to a slightly higher temperature than that used to promote scar tissue formation.

Figure 25:
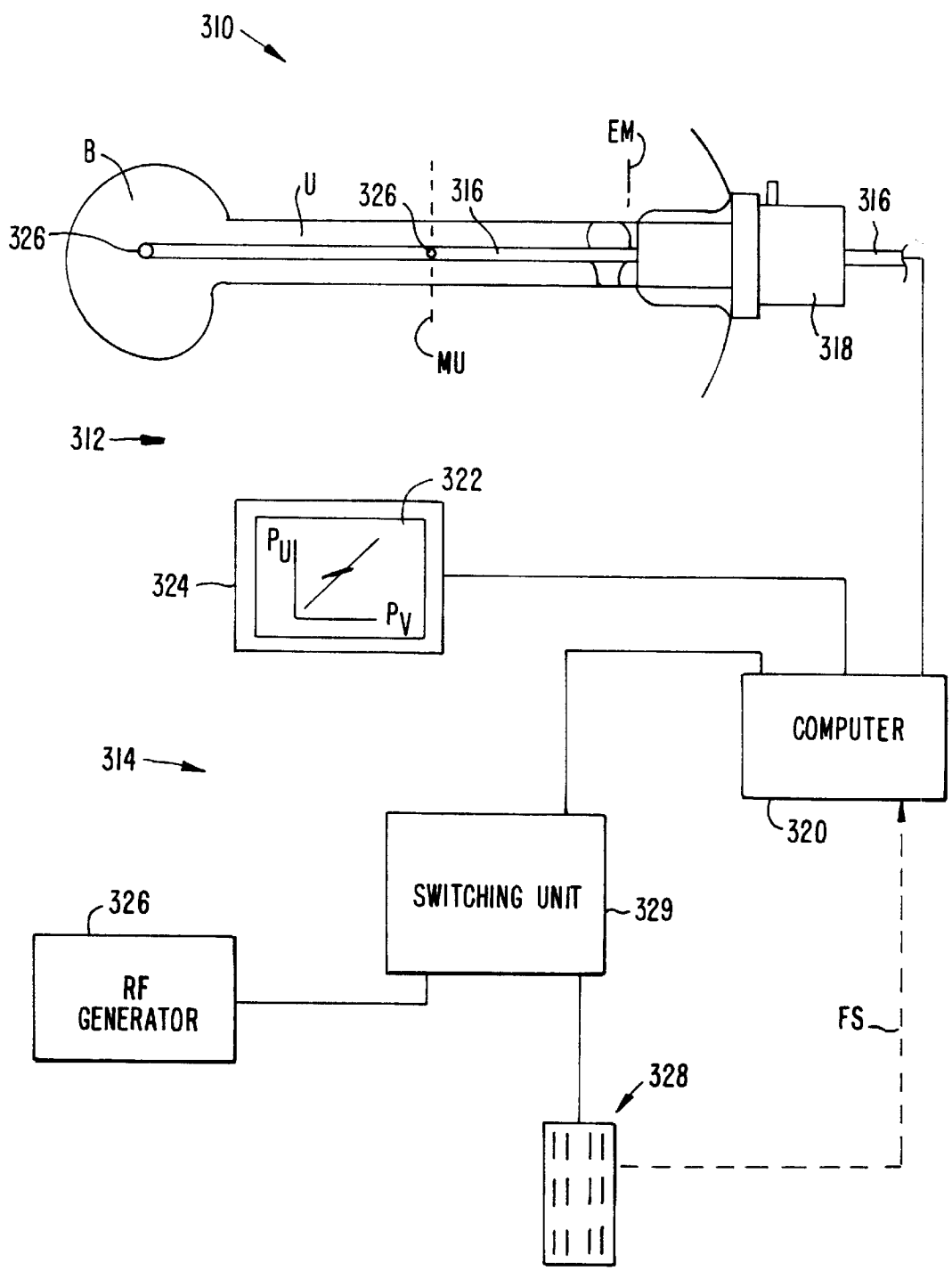
FIG. 25 illustrates an integrated diagnostic/treatment system for urinary incontinence.

Referring now to FIG. 25, a urinary incontinence diagnosis and treatment system 310 generally includes a diagnostic subsystem 312 for diagnosing stress incontinence and a treatment subsystem 314 which provides a therapy for a specific patient in response to a specific diagnosis. Diagnostic system 312 generally includes a catheter 316 for sensing pressures in bladder B and in urethra U, and a holder 318 which helps keep the catheter in position when the bladder and urethra move during a pressure pulse. Signals from catheter 316 are transmitted to processor 320, which displays a pressuregram 322 on display 324. Pressuregram 322 indicates a change in urethral pressure relative to a change in vesicular pressure.

As was described above, catheter 316 again includes pressure sensors 326. Pressure sensors 326 sense vesicular pressure within bladder B, and sense a maximum urethral pressure within urethra U, with the location of this maximum urethral pressure sometimes being referred to as the mid-urethra MU. To maintain the location of catheter 316 during a pressure pulse, holder 318 supports the catheter while allowing the catheter to move with the external meatus EM.

To maintain the position of catheter 316 within urethra U, the catheter may include a balloon which generally engages the surrounding urethra, or holder 318 may include a surface which engages, and which supports the catheter relative to, the external meatus EM. This allows catheter 316 to provide pressure signals which accurately reflect the urethral and vesicular pressure throughout a pressure pulse, which may be induced by having a patient cough, by applying an external impulse against the patient's abdomen, or the like. Processor 320 can record these pressures throughout multiple pressure pulses for displaying as pressuregram 322. Generally, where urethral pressure remains higher than vesicular pressure (above the $P_u=P_v$ line on the pressuregram) leakage will not occur. However, where vesicular pressure increases faster than urethral pressure during a pressure pulse, a sufficiently strong pulse may produce leakage.

To increase the rate of change of the urethral pressure for each increment of change in the vesicular pressure, treatment system 314 may be employed to increase a modulus of the patient's pelvic support system. Often, treatment system 314 will selectively promote formation of scar tissue along a fascial plane. To remodel tissues of the pelvic support system, power supply 326 directs RF current to selected pairs of electrodes on probe 328 under the direction of processor 320. Here, selective heating commands from processor 320 are implemented by a separate switching unit 329. It should be understood that in alternative arrangements, the switching unit may be incorporated into processor 320, power supply 326, or probe 328, and that separate processors may be provided for the diagnostic and treatment subsystems. In many embodiments, feedback on the course of treatment will be provided in the form of feedback signals FS transmitted from probe 328 to processor 320.

Figure 26A:
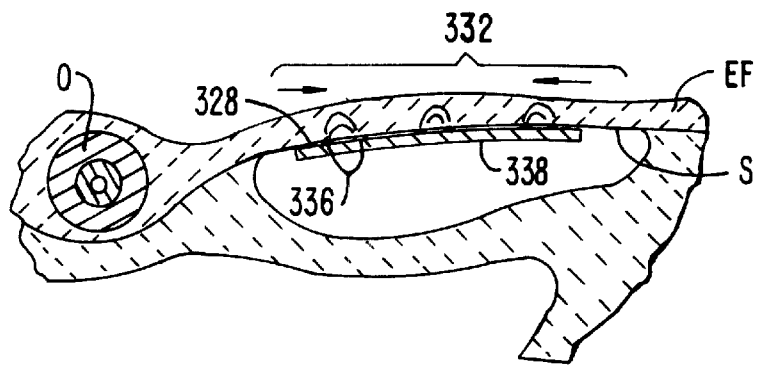
FIGS. 26A–C illustrate probes for treating incontinence and methods for their use.

The use of probe 328 of the system of FIG. 25 is illustrated in more detail in FIG. 26A. Probe 328 includes an array of electrode pairs 336 mounted to a probe body 338. Probe body 338 may optionally be supported on a shaft, which will typically contain the wires coupling electrode pairs 336 to power supply 326 (see FIG. 25). Electrode pairs 336 are selectively energized by the processor of system 310, so as to transmit sufficient energy to the endopelvic fascia to effect the desired treatment. Hence, processor 320 can tailor the treatment for a specific patient's diagnosis, for example, by varying the area of and energy delivered to target region 332 so as to selectively shrink and/or stiffen the endopelvic fascia layer sufficiently to maintain the urethral pressure above the vesicular pressure throughout a pressure pulse.

Electrodes 336 indirectly engage surface S of endopelvic fascia EF on either side of urethra U. Optionally, the probe may include temperature sensors so as to provide a feedback signal FS to processor 320 so as to maintain the temperature of the endopelvic fascia within a target temperature range. Optionally, the target temperature range may be sufficient to promote scar tissue formation and/or attachment of the endopelvic fascial layer, and may be insufficient to induce shrinkage of the endopelvic fascia. Alternatively, both scar tissue formation and shrinkage may be effected simultaneously. Preferably, probe 328 is used in a static position so that the treatment area is controlled by processor 320 via switching unit 329 selectively applying power to some or all of electrode pairs 336, the number and location of electrode pairs, the heat time, and the heat temperature being sufficient to achieve the desired result.

Figure 26B:
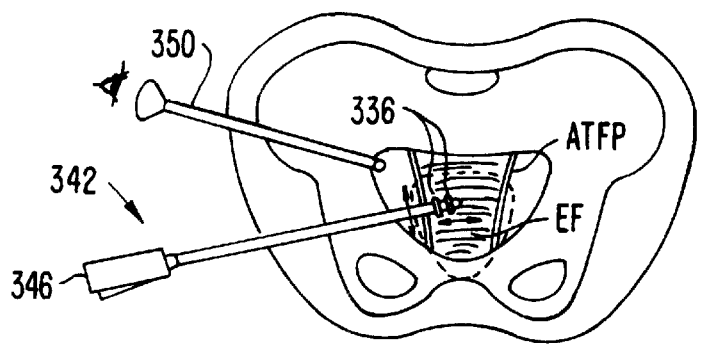

A laparoscopic device and method for directly heating endopelvic fascia EF can be understood with reference to FIG. 26B. Laparoscopic probe 342 includes a shaft supporting an electrode pair 336 relative to a handle. A variety of electrode pair configurations might be used. Preferably, a port will be disposed adjacent and/or between electrodes 336 to allow a small amount of irrigation flow before and/or during the treatment. This irrigation flow may comprise a conductive fluid such as saline or a nonconductive fluid, and will ideally be sufficient to avoid the accumulation of residue on the electrode pair surfaces. Laparoscopic probe 342 will generally be used in a laparoscopic procedure using a superior approach, typically under the direction of a laparoscope 350 inserted near the patient's mid-line (for example, adjacent the belly button). The handle 346 is manipulated so as to "paint" bipolar electrode 36 across the endopelvic fascia surface until the target region has been sufficiently heated.

Figure 26C:
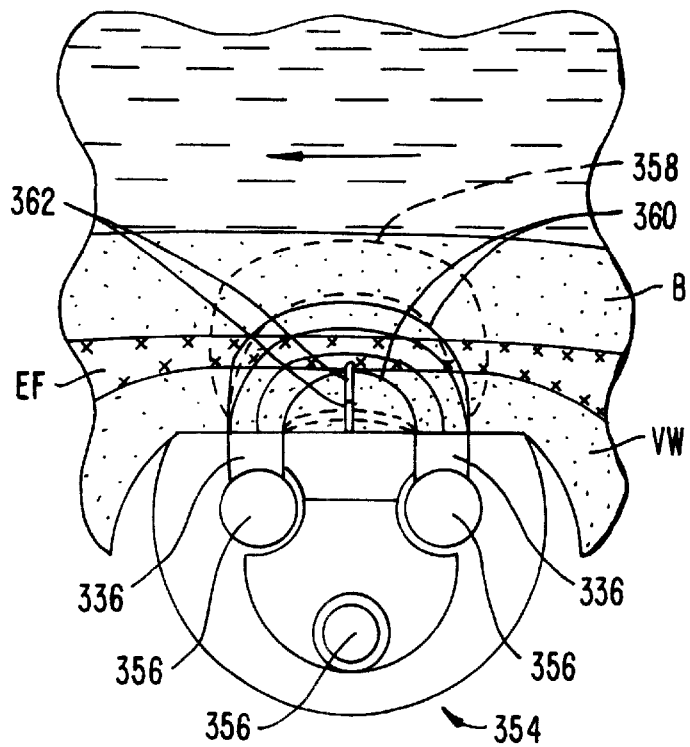

FIG. 26C illustrates a still further alternative probe for use with the system of FIG. 25. In this embodiment, a transvaginal bipolar probe 354 includes an electrode pair 336 which is cooled by fluid conduits 356. The fluid conduits cool the intervening tissue between bipolar probe 354 and endopelvic fascia EF via electrodes 336, and via the probe surface between the electrodes. Similarly, the tissue disposed beyond the endopelvic fascia (in this case a wall of bladder B) is cooled, here by circulation of a cooled solution within the bladder. Once the intervening tissue of the vaginal wall VW (and the bladder B beyond the target region of endopelvic fascia EF) are cooled sufficiently, RF current is transmitted between the electrodes to heat the endopelvic fascia. Advantageously, the pre-cooling can redirect the current flux 358 from the intervening and adjacent tissues to a desired flux pattern 360. Feedback on the precooling and heating temperatures may be provided by needle-mounted temperature sensors 362 mounted to the probe, and/or by temperature sensors mounted to the probe surface.

A variety of treatment modalities may be used to effect the desired tissue remodeling. Treatment modalities may include thermal, electrosurgical, laser, focused ultrasound and/or microwave, a variety of bioactive or biochemical agents including local drug delivery, caustic compounds, pleurodesis agents, sclerosing agents, growth factors, surgical sealants and/or the like. When bioactive agents are used, the invention may employ talcum, tetracycline and derivatives, bleomycin, sodium hydroxide, blood, mitomycin, doxycycline, mitoxatrone, dilute acids, absolute ethanol, silver nitrate, ethanolamine oleate, polidocanol, N-butyl-2-cyanoacrylate and/or any of a wide variety of available compounds being marketed.

While the exemplary embodiments of the present invention have been described in some detail, by way of example and for clarity of understanding, a variety of changes, modifications, and adaptations will be obvious to those of skill in the art. Hence, the scope of the present invention is limited solely by the appended claims.

What is claimed is:

1. An apparatus for evaluating urinary incontinence of a patient, the patient having a urethra extending from a bladder to a urethral opening with a maximum urethral pressure disposed therebetween, the system comprising:
a pressure-sensing system comprising an elongate body having a proximal end and a distal end, a vesicle pressure sensor disposed adjacent the distal end for measuring fluid pressure within the bladder, and at least one urethral pressure sensor disposed proximally of the vesicle pressure sensor for measuring urethral pressure;
an anchoring structure disposed along the elongate body, the anchoring structure adapted to engage a tissue surface comprising or adjacent the urethra so as to maintain alignment between the urethral pressure sensor and the maximum urethral pressure when a pressure pulse moves the urethra; and
a processor coupled to the pressure-sensing system, the processor calculating a relationship between the urethral pressure and the vesicle pressure.

2. The apparatus of claim 1, wherein the relationship comprises a pressuregram, and further comprising a display showing the pressuregram in real time to a system operator disposed adjacent the patient, the pressuregram comprising a slope defined by an increase of the measured vesicle pressure relative to an increase of the measured urethral pressure.

3. The apparatus of claim 1, wherein the relationship is calculated from a plurality of pressure pulses.

4. The apparatus of claim 1, wherein the relationship is independent of time.

5. The apparatus of claim 1, wherein the anchoring structure comprises a radially expandable structure.

6. The apparatus of claim 5, wherein the anchoring structure is disposed proximally of the vesicle pressure sensor and has at least one axial channel, the channel allowing free transmission of urine through the urethra when the expandable structure is expanded to inhibit movement of the sensor system relative to the urethra.

7. The apparatus of claim 6, wherein the expandable structure comprises a balloon having an inflated cross-section defining the at least one channel.

8. The apparatus of claim 5, wherein the expandable structure is disposed distally of the at least one urethral pressure sensor and has a proximally oriented surface for engaging the bladder adjacent the urethra, the at least one pressure sensor capable of measuring the maximum urethral pressure at a variable distance from the expandable structure, the anchoring structure further comprising a distally oriented tissue-engaging surface positionable along the elongate body for engaging an external meatus adjacent the urethral opening so as to axially affix the urethral pressure sensor relative to the maximum urethral pressure between the distally oriented surface and the proximally oriented surface.

9. The apparatus of claim 1, wherein the anchoring structure comprises a distally oriented surface adapted for engaging an external meatus adjacent the urethral opening, the distally oriented surface variably positionable relative to the urethral pressure sensor for alignment of the urethral pressure sensor with the maximum urethral pressure.

10. The apparatus of claim 9, further comprising a support longitudinally movable relative to the distally oriented surface, and a biasing device coupling the support relative the distally oriented surface to urge the distally oriented surface distally against the external meatus.

11. The apparatus of claim 1, wherein the anchoring structure comprises at least one vacuum port oriented to engage a tissue along the urethra so as to inhibit movement of the urethral pressure sensor relative to the maximum urethral pressure.

12. The apparatus of claim 11, wherein the anchoring structure further comprises a vacuum system coupled to the vacuum port.

13. The apparatus of claim 1, wherein at least one of the sensors comprises a port coupled to a transducer by a fluid lumen.

14. The apparatus of claim 1, wherein at least one of the sensors comprises a piezo-resistive transducer or an optical pressure sensor.

15. The apparatus of claim 1, wherein the at least one urethral pressure sensor comprises a plurality of axially separated sensors exposed to a plurality of differing urethral pressures, the processor selectively couplable to each sensor so as to calculate the relationship when the maximum urethral pressure moves between the plurality of urethral pressure sensors.

16. An apparatus for evaluating urinary incontinence of a patient, the patient having a urethra extending from a bladder to a urethral opening with a maximum urethral pressure disposed therebetween, the system comprising:
a pressure-sensing system comprising an elongate body having a proximal end and a distal end, a vesicle pressure sensor disposed adjacent the distal end for measuring fluid pressure within the bladder, and at least one urethral pressure sensor disposed proximally of the vesicle pressure sensor for measuring urethral pressure;
anchoring means disposed along the elongate body for contacting a tissue surface comprising or adjacent the urethra so as to maintain alignment between the urethral pressure sensor and the maximum urethral pressure when a pressure pulse moves the urethra; and
processor means coupled to the pressure-sensing system for calculating a relationship between the urethral pressure and the vesicle pressure.

17. The apparatus of claim 16 wherein the radially expandable anchoring structure is on communication with at least one channel, the channel allowing free transmission of urine through the urethra when the expandable structure is expanded to inhibit movement of the sensor system relative to the urethra.

18. The apparatus of claim 16 wherein a distal surface of the radially expandable anchoring structure is positionable on the body to contact an external meatus so as to substantially affix the urethral pressure sensor relative to the maximum urethral pressure.

19. An apparatus for evaluating urinary incontinence of a patient, the patient having a urethra extending from a bladder to a urethral opening with a maximum urethral pressure disposed therebetween, the system comprising:
a pressure-sensing system comprising a body having a proximal end and a distal end, a vesicle pressure sensor disposed adjacent the distal end for measuring fluid pressure within the bladder, and at least one urethral pressure sensor disposed proximally of the vesicle pressure sensor for measuring urethral pressure;

a radially expandable anchoring structure disposed along the body, the anchoring structure adapted to engage a tissue surface comprising or adjacent the urethra so as to maintain alignment between the urethral pressure sensor and the maximum urethral pressure when a pressure pulse moves the urethra; and a processor coupled to the pressure-sensing system, the processor calculating a relationship between the urethral pressure and the vesicle pressure.

20. An apparatus for evaluating urinary incontinence of a patient, the patient having a urethra extending from a bladder to a urethral opening with a maximum urethral pressure disposed therebetween, the system comprising:

a pressure-sensing system comprising a body having a proximal end and a distal end, a vesicle pressure sensor disposed adjacent the distal end for measuring fluid pressure within the bladder, and at least one urethral pressure sensor disposed proximally of the vesicle pressure sensor for measuring urethral pressure;

a vacuum anchoring structure disposed along the body, the anchoring structure adapted to engage a tissue surface comprising or adjacent the urethra so as to maintain alignment between the urethral pressure sensor and the maximum urethral pressure when a pressure pulse moves the urethra; and a processor coupled to the pressure-sensing system, the processor calculating a relationship between the urethral pressure and the vesicle pressure.

21. The apparatus of claim 20 wherein the vacuum anchoring structure comprises at least one vacuum port that is oriented to engage a tissue along the urethra.

* * * * *